United States Patent
Koenig et al.

(10) Patent No.: US 10,828,115 B2
(45) Date of Patent: Nov. 10, 2020

(54) ROBOTIC ARM AND ROBOTIC SURGICAL SYSTEM

(71) Applicant: SRI INTERNATIONAL, Menlo Park, CA (US)

(72) Inventors: Karen Shakespear Koenig, San Jose, CA (US); Pablo Eduardo Garcia Kilroy, Menlo Park, CA (US); Sina Nia Kosari, Fremont, CA (US); Thomas D. Egan, Marblehead, MA (US)

(73) Assignee: SRI International, Menlo Park, CA (US)

( * ) Notice: Subject to any disclaimer, the term of this patent is extended or adjusted under 35 U.S.C. 154(b) by 669 days.

(21) Appl. No.: 15/217,446

(22) Filed: Jul. 22, 2016

(65) Prior Publication Data

US 2017/0020615 A1     Jan. 26, 2017

Related U.S. Application Data

(60) Provisional application No. 62/196,190, filed on Jul. 23, 2015.

(51) Int. Cl.
*A61B 34/30*     (2016.01)
*A61B 34/00*     (2016.01)
(Continued)

(52) U.S. Cl.
CPC ............ *A61B 34/30* (2016.02); *A61B 34/37* (2016.02); *A61B 34/72* (2016.02); *A61B 46/10* (2016.02);
(Continued)

(58) Field of Classification Search
CPC ...... A61B 34/37; A61B 2034/301; B25J 9/06; B25J 9/106
See application file for complete search history.

(56) References Cited

U.S. PATENT DOCUMENTS

| | | | |
|---|---|---|---|
| 4,843,921 A | 7/1989 | Kremer | |
| 5,339,723 A | 8/1994 | Huitema | |

(Continued)

FOREIGN PATENT DOCUMENTS

| | | |
|---|---|---|
| EP | 2415418 | 2/2012 |
| GB | 2523224 | 8/2015 |

(Continued)

OTHER PUBLICATIONS

International Search Report and Written Opinion dated Aug. 18, 2014 in PCT Application No. PCT/US2014/026721.

(Continued)

*Primary Examiner* — Sarah W Aleman

(74) *Attorney, Agent, or Firm* — McDonnell Boehnen Hulbert & Berghoff LLP

(57) ABSTRACT

A robotic arm according to various implementations includes: a tool driver configured to hold a surgical tool; a first section comprising a first end coupled to a base, a second end distal from first end; a first link that includes a motor configured to rotate at least a portion of the first section around a pitch axis; a second link coupled to the first link, the second link including a motor configured to rotate at least a portion of the first section around a roll axis; and a second section comprising: a first end coupled to the second end of the first section, a second end distal from the first end, a first link that includes a motor configured to rotate at least a portion of the second section around a roll axis, a second link coupled to the first link.

18 Claims, 14 Drawing Sheets

(51) Int. Cl.

| | | |
|---|---|---|
| *A61B 34/37* | (2016.01) | |
| *A61B 46/10* | (2016.01) | |
| *B25J 3/04* | (2006.01) | |
| *B25J 9/10* | (2006.01) | |
| *B25J 9/06* | (2006.01) | |
| *B25J 9/00* | (2006.01) | |
| *B25J 9/12* | (2006.01) | |
| *B25J 13/02* | (2006.01) | |
| *B25J 13/08* | (2006.01) | |
| *B25J 17/02* | (2006.01) | |
| *A61B 17/34* | (2006.01) | |
| *A61B 17/00* | (2006.01) | |
| *A61B 17/29* | (2006.01) | |

(52) U.S. Cl.
CPC ............... *B25J 3/04* (2013.01); *B25J 9/0027* (2013.01); *B25J 9/0039* (2013.01); *B25J 9/06* (2013.01); *B25J 9/104* (2013.01); *B25J 9/12* (2013.01); *B25J 13/02* (2013.01); *B25J 13/085* (2013.01); *B25J 17/0283* (2013.01); *A61B 17/34* (2013.01); *A61B 2017/00327* (2013.01); *A61B 2017/00477* (2013.01); *A61B 2017/2919* (2013.01); *A61B 2017/2923* (2013.01); *A61B 2017/2927* (2013.01); *A61B 2017/2932* (2013.01); *A61B 2034/302* (2016.02); *A61B 2034/303* (2016.02); *A61B 2034/742* (2016.02); *G05B 2219/45117* (2013.01)

(56) References Cited

U.S. PATENT DOCUMENTS

| | | |
|---|---|---|
| 5,720,742 A | 2/1998 | Zacharias |
| 5,855,583 A | 1/1999 | Wang et al. |
| 5,943,914 A * | 8/1999 | Morimoto ............... A61B 34/76 414/2 |
| 6,270,508 B1 | 8/2001 | Klieman et al. |
| 6,331,181 B1 | 12/2001 | Tierney et al. |
| 6,450,978 B1 | 9/2002 | Brosseau et al. |
| 6,451,027 B1 | 9/2002 | Cooper et al. |
| 6,459,926 B1 | 10/2002 | Nowlin et al. |
| 6,471,642 B1 | 10/2002 | Igarashi |
| 6,490,490 B1 | 12/2002 | Uchikubo et al. |
| 6,491,701 B2 | 12/2002 | Tierney et al. |
| 6,522,906 B1 | 2/2003 | Salisbury et al. |
| 6,535,756 B1 | 3/2003 | Simon et al. |
| 6,582,358 B2 | 6/2003 | Akui et al. |
| 6,587,750 B2 | 7/2003 | Gerbi et al. |
| 6,608,628 B1 | 8/2003 | Ross et al. |
| 6,659,939 B2 | 12/2003 | Moll et al. |
| 6,669,635 B2 | 12/2003 | Kessman et al. |
| 6,682,478 B2 | 1/2004 | Nakamura |
| 6,793,625 B2 | 9/2004 | Cavallaro et al. |
| 6,799,065 B1 | 9/2004 | Niemeyer |
| 6,892,090 B2 | 5/2005 | Verard et al. |
| 6,951,535 B2 | 10/2005 | Ghodoussi et al. |
| 6,962,581 B2 | 11/2005 | Thoe |
| 6,995,744 B1 | 2/2006 | Moore et al. |
| 7,008,362 B2 | 3/2006 | Fitzgibbon |
| 7,012,203 B2 | 3/2006 | Hanson et al. |
| 7,046,270 B2 | 5/2006 | Murata et al. |
| 7,048,745 B2 | 5/2006 | Tierney et al. |
| 7,076,286 B2 | 7/2006 | Mizoguchi et al. |
| 7,101,334 B2 | 9/2006 | Takahashi |
| 7,106,479 B2 | 9/2006 | Roy et al. |
| 7,206,627 B2 | 4/2007 | Abovitz et al. |
| 7,217,269 B2 | 5/2007 | El-Galley et al. |
| 7,277,120 B2 | 10/2007 | Gere et al. |
| 7,317,955 B2 | 1/2008 | McGreevy |
| 7,319,466 B1 | 1/2008 | Tarr et al. |
| 7,369,116 B2 | 5/2008 | Logue |
| 7,379,790 B2 | 5/2008 | Toth et al. |
| 7,417,665 B2 | 8/2008 | Banju et al. |
| 7,498,532 B2 | 3/2009 | Kuhner et al. |
| 7,524,320 B2 | 4/2009 | Tierney et al. |
| 7,671,888 B2 | 3/2010 | Nogami et al. |
| 7,683,926 B2 | 3/2010 | Schechterman et al. |
| 7,768,702 B2 | 8/2010 | Hirose et al. |
| 7,781,941 B2 | 8/2010 | Horvath et al. |
| 7,783,133 B2 | 8/2010 | Dunki-Jacobs et al. |
| 7,789,874 B2 | 9/2010 | Yu et al. |
| 7,789,875 B2 | 9/2010 | Brock et al. |
| 7,806,891 B2 | 10/2010 | Nowlin et al. |
| 7,840,042 B2 | 11/2010 | Kriveshko et al. |
| 7,843,158 B2 | 11/2010 | Prisco |
| 7,865,266 B2 | 1/2011 | Moll et al. |
| 7,883,458 B2 | 2/2011 | Hamel |
| 7,907,166 B2 | 3/2011 | Lamprecht et al. |
| 7,947,050 B2 | 5/2011 | Lee et al. |
| 7,955,322 B2 | 6/2011 | Devengenzo et al. |
| 7,979,157 B2 | 7/2011 | Anvari |
| 7,983,793 B2 | 7/2011 | Toth et al. |
| 8,004,229 B2 * | 8/2011 | Nowlin .................. B25J 9/1682 318/568.21 |
| 8,062,288 B2 | 11/2011 | Cooper et al. |
| 8,079,950 B2 | 12/2011 | Stern et al. |
| 8,086,008 B2 | 12/2011 | Coste-Maniere et al. |
| 8,095,200 B2 | 1/2012 | Quaid et al. |
| 8,118,805 B2 | 2/2012 | Jinno et al. |
| 8,126,114 B2 | 2/2012 | Naylor et al. |
| 8,131,031 B2 | 3/2012 | Lloyd |
| 8,142,447 B2 | 3/2012 | Cooper et al. |
| 8,147,503 B2 | 4/2012 | Zhao et al. |
| 8,155,479 B2 | 4/2012 | Hoffman et al. |
| 8,190,238 B2 | 5/2012 | Moll et al. |
| 8,206,406 B2 | 6/2012 | Orban et al. |
| 8,256,319 B2 | 9/2012 | Cooper et al. |
| 8,266,979 B2 * | 9/2012 | Yonehara ................. B25J 9/046 74/490.02 |
| 8,284,234 B2 | 10/2012 | Bjelkhagen et al. |
| 8,332,072 B1 | 12/2012 | Schaible et al. |
| 8,398,541 B2 | 3/2013 | DiMaio et al. |
| 8,442,686 B2 * | 5/2013 | Saito ........................ B25J 9/06 700/245 |
| 8,469,947 B2 | 6/2013 | Devengenzo et al. |
| 8,473,031 B2 | 6/2013 | Nixon et al. |
| 8,504,136 B1 | 8/2013 | Sun et al. |
| 8,506,555 B2 | 8/2013 | Morales |
| 8,508,173 B2 | 8/2013 | Goldberg et al. |
| 8,521,331 B2 | 8/2013 | Itkowitz |
| 8,527,094 B2 | 9/2013 | Kumar et al. |
| 8,562,594 B2 | 10/2013 | Cooper et al. |
| 8,594,841 B2 | 11/2013 | Zhao et al. |
| 8,600,551 B2 | 12/2013 | Itkowitz et al. |
| 8,634,957 B2 | 1/2014 | Toth et al. |
| 8,638,056 B2 | 1/2014 | Goldberg et al. |
| 8,648,896 B2 | 2/2014 | Takahashi |
| 8,672,922 B2 | 3/2014 | Loh et al. |
| 8,682,489 B2 | 3/2014 | Itkowitz et al. |
| 8,706,184 B2 | 4/2014 | Mohr et al. |
| 8,712,115 B2 | 4/2014 | Kirchberg et al. |
| 8,747,288 B2 | 6/2014 | Strotzer et al. |
| 8,749,190 B2 | 6/2014 | Nowlin et al. |
| 8,761,337 B2 | 6/2014 | Naylor et al. |
| 8,806,359 B2 | 8/2014 | Garibaldi et al. |
| 8,828,023 B2 | 9/2014 | Neff et al. |
| 8,831,782 B2 | 9/2014 | Itkowitz |
| 8,888,764 B2 | 11/2014 | Devengenzo et al. |
| 8,930,027 B2 | 1/2015 | Schaible et al. |
| 8,939,500 B2 | 1/2015 | Voigt et al. |
| 8,989,903 B2 | 3/2015 | Weir et al. |
| 8,996,173 B2 | 3/2015 | Itkowitz et al. |
| 9,002,517 B2 | 4/2015 | Bosscher et al. |
| 9,026,247 B2 | 5/2015 | White et al. |
| 9,068,824 B2 | 6/2015 | Findeisen et al. |
| 9,101,267 B2 | 8/2015 | Umasuthan et al. |
| 9,108,318 B2 | 8/2015 | Diolaiti |
| 9,129,422 B2 | 9/2015 | Mountney et al. |
| 9,138,135 B2 | 9/2015 | Oderwald et al. |
| 9,161,681 B2 | 10/2015 | Galstian et al. |
| 9,179,980 B2 | 11/2015 | Yoon |

(56) References Cited

U.S. PATENT DOCUMENTS

| | | | |
|---|---|---|---|
| 9,192,286 B2 | 11/2015 | Kazakevich et al. | |
| 9,198,731 B2 | 12/2015 | Balaji et al. | |
| 9,215,293 B2 | 12/2015 | Miller | |
| 9,221,172 B2 | 12/2015 | Williamson et al. | |
| 9,232,984 B2 | 1/2016 | Guthart et al. | |
| 9,241,768 B2 | 1/2016 | Sandhu et al. | |
| 9,254,078 B2 | 2/2016 | McDowall | |
| 9,254,572 B2 | 2/2016 | Strotzer | |
| 9,256,936 B2 | 2/2016 | Jacobs et al. | |
| 9,259,276 B2 | 2/2016 | Mintz et al. | |
| 9,259,282 B2 | 2/2016 | Azizian et al. | |
| 9,345,544 B2 | 5/2016 | Hourtash et al. | |
| 2002/0082612 A1 | 6/2002 | Moll et al. | |
| 2004/0106916 A1 | 6/2004 | Quaid et al. | |
| 2004/0199147 A1 | 10/2004 | Nishizawa | |
| 2004/0243147 A1 | 12/2004 | Lipow | |
| 2007/0089557 A1* | 4/2007 | Solomon | B25J 9/1045 74/490.01 |
| 2008/0154246 A1 | 6/2008 | Nowlin et al. | |
| 2009/0192519 A1 | 7/2009 | Omori | |
| 2010/0004663 A1 | 1/2010 | Murphy et al. | |
| 2010/0016852 A1 | 1/2010 | Manzo et al. | |
| 2010/0175701 A1 | 7/2010 | Reis et al. | |
| 2010/0198253 A1 | 8/2010 | Jinno et al. | |
| 2011/0118752 A1 | 5/2011 | Itkowitz et al. | |
| 2012/0011956 A1* | 1/2012 | Lundberg | B25J 9/04 74/490.03 |
| 2012/0130399 A1 | 5/2012 | Moll et al. | |
| 2012/0277663 A1 | 11/2012 | Millman et al. | |
| 2012/0316681 A1 | 12/2012 | Hagn et al. | |
| 2013/0030448 A1 | 1/2013 | Cooper et al. | |
| 2013/0063580 A1 | 3/2013 | Ogawa et al. | |
| 2014/0100588 A1 | 4/2014 | Blumenkranz et al. | |
| 2014/0171965 A1 | 6/2014 | Loh et al. | |
| 2014/0188131 A1 | 7/2014 | Toth et al. | |
| 2015/0025549 A1 | 1/2015 | Kilroy et al. | |
| 2015/0038981 A1 | 2/2015 | Kilroy et al. | |
| 2015/0038982 A1 | 2/2015 | Kilroy et al. | |
| 2015/0150635 A1 | 6/2015 | Kilroy et al. | |
| 2015/0209965 A1 | 7/2015 | Low et al. | |
| 2015/0321355 A1 | 11/2015 | Kishi | |

FOREIGN PATENT DOCUMENTS

| | | |
|---|---|---|
| SE | 525399 C2 | 2/2005 |
| WO | 2011060185 | 5/2011 |
| WO | 2014084408 | 6/2014 |
| WO | 2014151621 | 9/2014 |
| WO | 2014151952 | 9/2014 |
| WO | 2017/015599 A1 | 1/2017 |

OTHER PUBLICATIONS

International Search Report and Written Opinion dated Aug. 21, 2014 in PCT Application No. PCT/US2014/026115.
International Preliminary Report on Patentability dated Sep. 15, 2015 in PCT Application No. PCT/US2014/026115.
International Preliminary Report on Patentability dated Sep. 15, 2015 in PCT Application No. PCT/US2014/026721.
International Search Report and Written Opinion dated Nov. 2, 2015 in PCT Application No. PCT/US2015/042991.
International Search Report and Written Opinion dated Jan. 7, 2016 in PCT Application No. PCT/US2015/052354.
Supplemental Partial European Search Report dated Mar. 9, 2016 in EP Application No. 14770569.
Supplemental European Search Report dated Mar. 10, 2016 in EP Application No. 14767688.
Supplemental European Search Report dated Jun. 29, 2016 in EP Application No. 14770569.
Written Opinion of the International Search Authority dated Nov. 30, 2016 for WO Application No. PCT/US16/043666.
Outgoing—ISA/210—International Search Report dated Nov. 30, 2016 for WO Application No. PCT/US16/043666.
(IPEA/409) International Preliminary Report on Patentability Chapter II or (IB/373) International Preliminary Report on Patentability Chapter I dated Feb. 1, 2018 for WO Application No. PCT/US16/043666.
Search Report and Written Opinion issued in related application PCT/US2016/043666, dated Nov. 30, 2016, 16 pages.

* cited by examiner

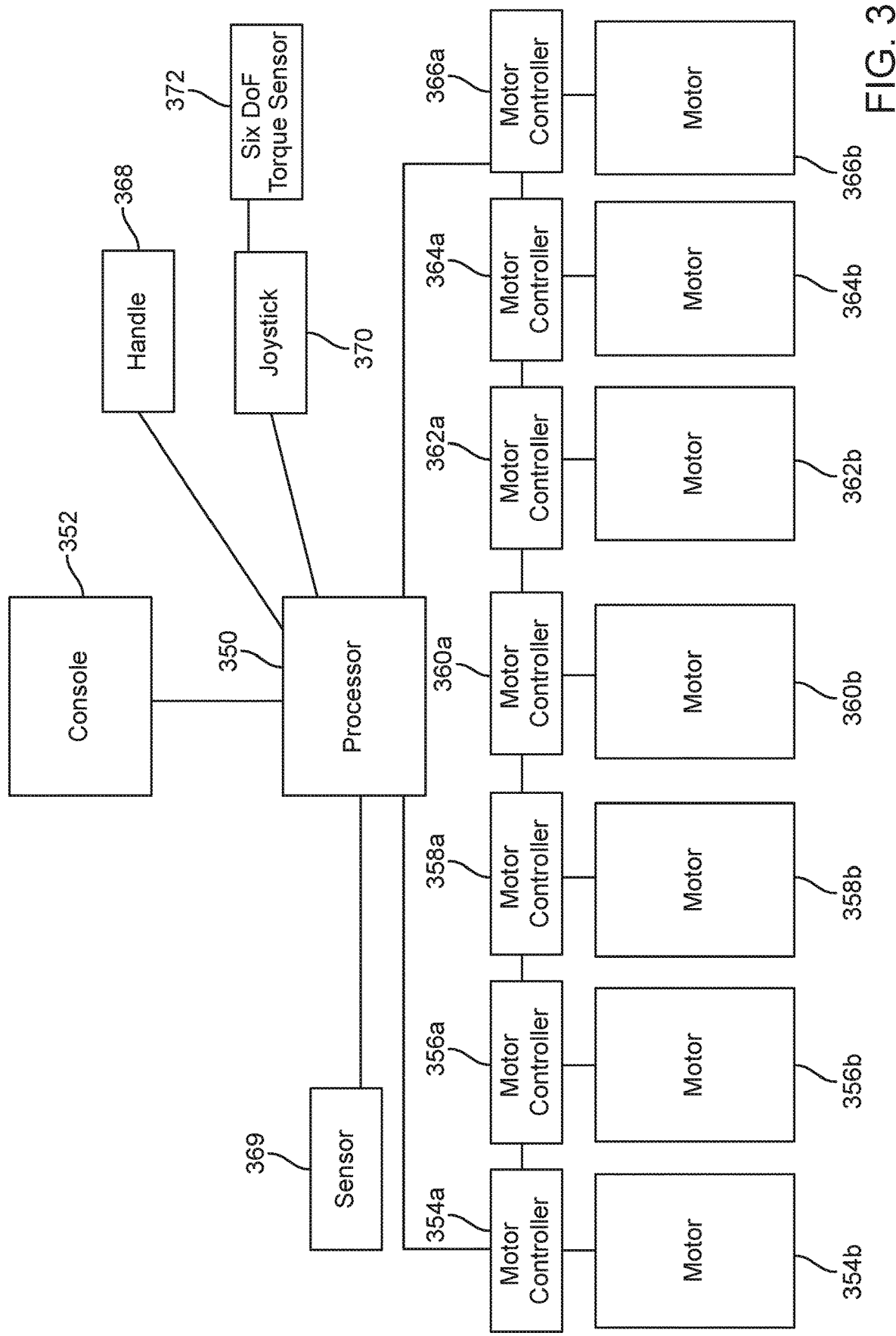

ROBOTIC ARM AND ROBOTIC SURGICAL SYSTEM

CROSS-REFERENCE TO RELATED APPLICATIONS

This application claims the priority benefit of U.S. Provisional Application No. 62/196,190, filed Jul. 23, 2015 and incorporated herein by reference.

TECHNICAL FIELD

This disclosure relates generally to robotic surgery and, more particularly, to a robotic arm and a robotic surgical system.

BACKGROUND

Robot-assisted surgery (often referred to as "robotic surgery") has become widespread in the past few years, with tens of thousands of procedures being performed every year. Robotic surgical systems have been deployed successfully in hospitals and other medical facilities throughout the world and represent a major technological advance in the field of medicine. However, existing systems can be difficult to set up and manage. Furthermore, they tend to be very costly.

DRAWINGS

While the appended claims set forth the features of the present techniques with particularity, these techniques may be best understood from the following detailed description taken in conjunction with the accompanying drawings of which:

FIG. 3 is a block diagram showing a processor in communication with a console and with motor controllers of the various motors of the robotic arm, according to an embodiment.

DESCRIPTION

Figure 1A:
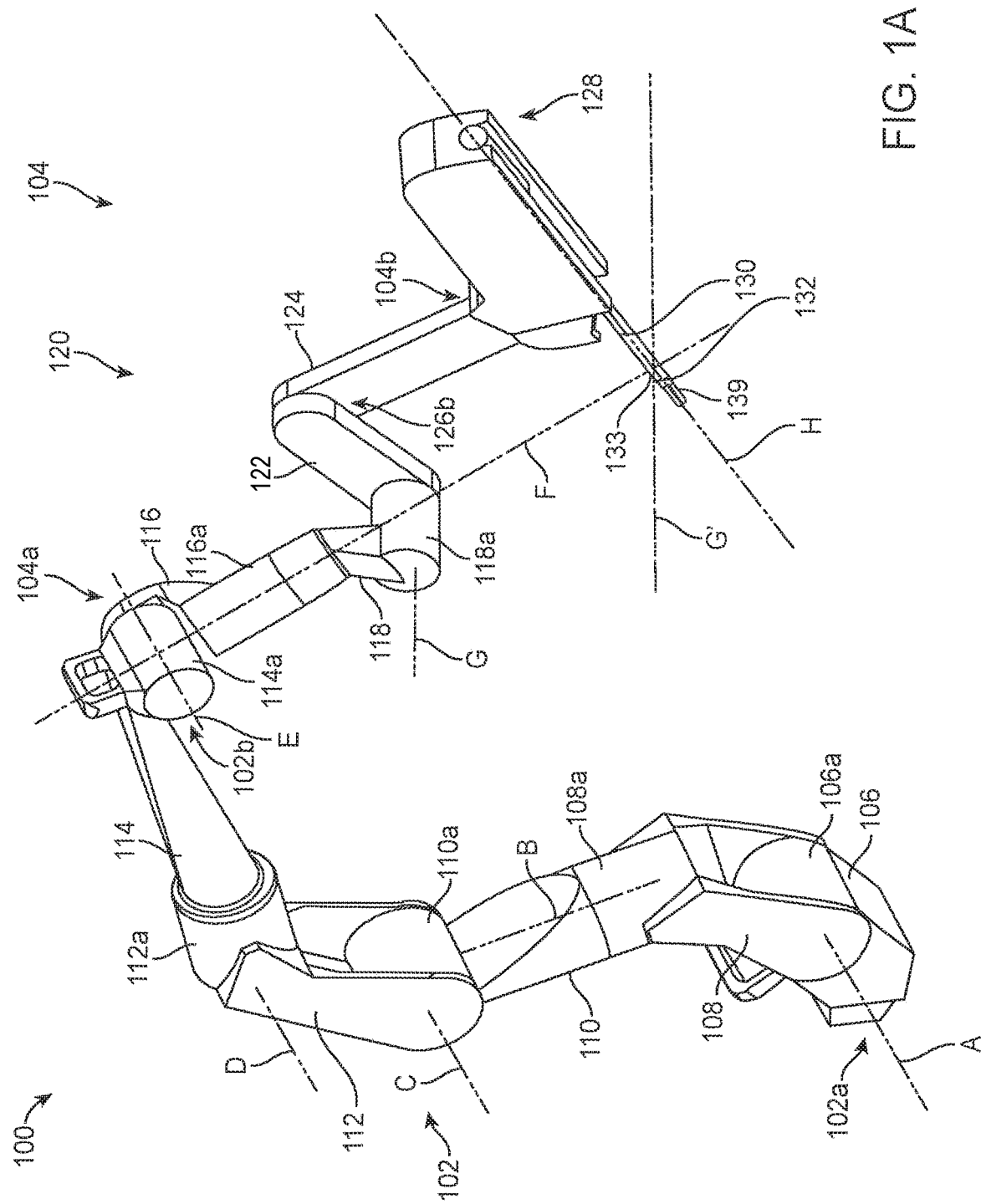
FIGS. 1A and 1B are elevated views of a robotic arm according to various embodiments.
Figure 1B:
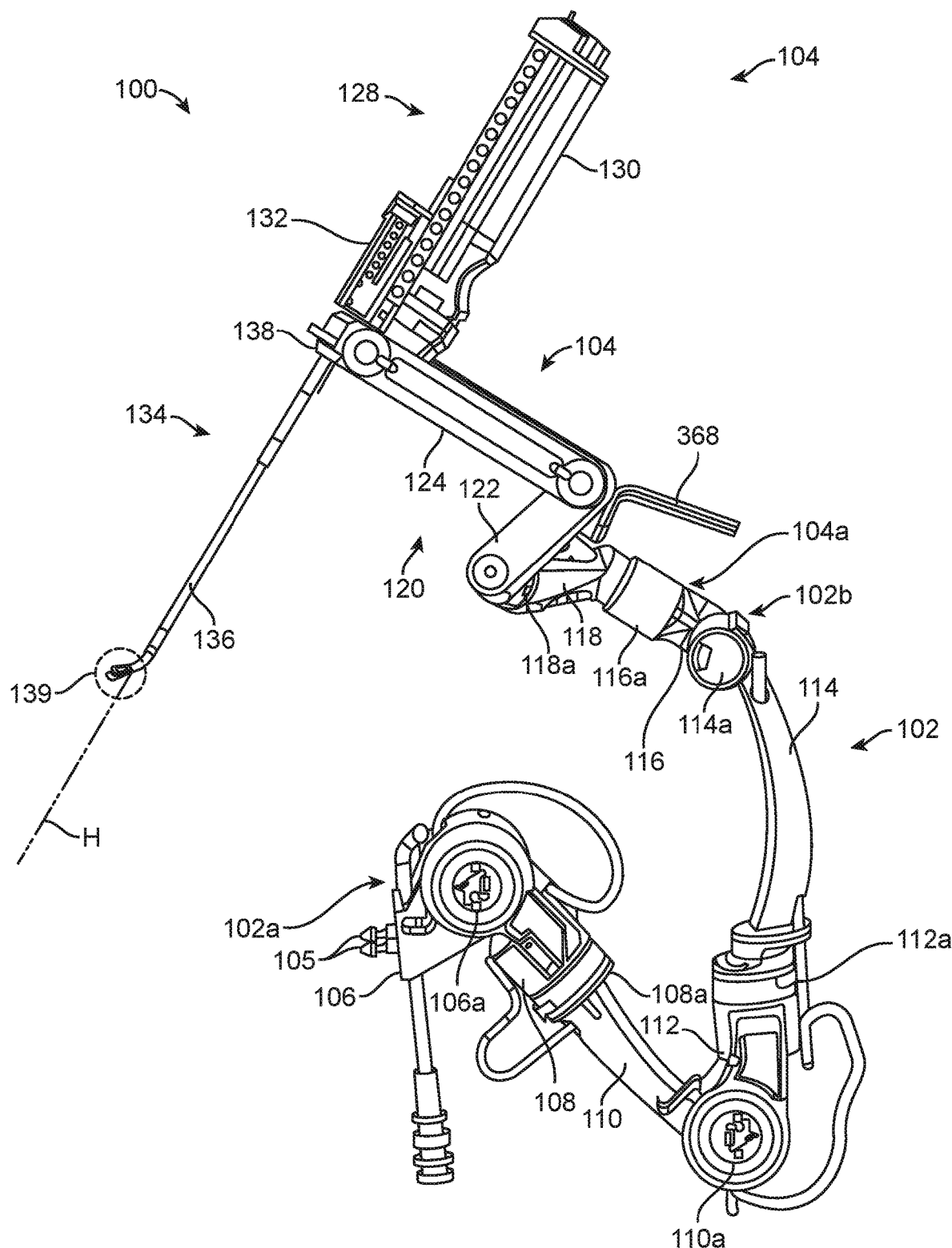

This disclosure is generally directed to a robotic arm and robotic surgical system. Turning to FIG. 1A and FIG. 1B, embodiments of the robotic arm are shown. The robotic arm, generally labelled 100, includes a first section 102 and a second section 104. The first section 102 has a first end 102a and a second end 102b. The second section 104 has a first end 104a and a second end 104b. The robotic arm 100 ("arm 100") also includes a pitch assembly 120 coupled to the second end 104b of the second section 104 and a tool driver 128 coupled to the pitch assembly 120.

The first end 102a of the first section 102 is coupled to a stationary (or relatively stationary) structure (such as a surgical table) and may be referred to as the first end of the arm 100. The second end 104b of the second section 104 may be referred to as the second end of the arm 100. Also, the first section 102 may be referred to herein as a "Cartesian arm 102" because (as will be described below) the first section 102 may be used to move the second section 104 into position (e.g., using xyz coordinates in a three dimensional space) at a surgical site on a patient's body. The second section 104 may sometimes be referred to herein as a "spherical arm 104."

The first section 102 includes a first link 106, a second link 108, a third link 110, a fourth link 112, and a fifth link 114. In the embodiments illustrated in FIG. 1A and FIG. 1B, these links are implemented as, and may be referred to herein as a base link 106, a shoulder pitch link 108, a shoulder roll link 110, an elbow link 112, and a forearm link 114. The base link 106 is configured to be removeably attached to a structure, such as a surgical table (e.g., via mounting pins 105, shown in FIG. 1B). Each link has a proximal end (the end coupled closest to the first end 102a of the first section 102) and a distal end (the end coupled furthest from the first end 102a).

The second section 104 includes first link 116, a second link 118, and a pitch assembly 120. The pitch assembly 120 includes first link 122 and a second link 124. In the embodiments illustrated in FIG. 1A and FIG. 1B, the various links of the second section 104 are implemented as, and may be referred to herein as a spherical arm base link 116, a spherical arm roll link 118, pitch A link 122, and pitch B link 124.

The links of the first section 102 and the second section 104 may be made of any of a variety materials and may be of unibody construction or of multiple discrete components assembled together by welding, screwing, laminating, etc. The links may be of a variety of shapes (e.g., clevis-shaped).

The base link 106 includes a housing 106a that contains a first motor. The shoulder pitch link 108 is rotatably coupled to the base link 106. The shaft of the first motor is attached to the shoulder pitch link 108 and defines a first joint having an axis of rotation A (shown in FIG. 1A) ("axis A"), such that when the first motor rotates its shaft, the shoulder pitch link 108 pivots about axis A in a corresponding manner.

The shoulder pitch link 108 includes a housing 108a that contains a second motor. The shoulder roll link 110 is rotatably coupled to the shoulder pitch link 108. The shaft of the second motor is attached to the shoulder roll link 110 and defines a second joint having an axis of rotation B ("axis B") so that when the second motor rotates its shaft, the shoulder roll link 110 rolls about axis B in a corresponding manner.

The shoulder roll link 110 includes a housing 110a that contains a third motor. The elbow link 112 is rotatably coupled to the shoulder roll link 110. The shaft of the third motor is attached to the elbow link 112 and defines a third joint having an axis of rotation C ("axis C") so that when the third motor rotates its shaft, the elbow link 112 pivots about axis C in a corresponding manner.

The elbow link 112 includes a housing 112a that contains a fourth motor. The forearm link 114 is rotatably coupled to the elbow link 112. The shaft of the fourth motor is attached to the elbow link 112 and defines a fourth joint having an axis of rotation D ("axis D") so that when the fourth motor rotates its shaft, the forearm link 114 rolls about axis D in a corresponding manner.

The forearm link 114 includes a housing 114a (located at the second end 102b of the first section 102) that contains a fifth motor. The spherical arm base link 116 is rotatably coupled to the forearm link 114 (and, therefore, to the second end 102b of the first section 102). The shaft of the fifth motor is attached to the spherical arm base link 116 and defines a fifth joint having an axis of rotation E ("axis E") so that when the fifth motor rotates its shaft, the spherical arm base link 116 (and, consequently, the entire spherical arm 104) pivots about axis E.

The spherical arm base link 116 includes a housing 116a that contains a sixth motor. The spherical arm roll link 118 is rotatably coupled to the spherical arm base link 116. The shaft of the sixth motor is attached to the spherical arm roll link 118 and defines a sixth joint having an axis of rotation F ("axis F") so that when the sixth motor rotates its shaft, spherical arm roll link 118 rolls about axis F.

The spherical arm roll link 118 includes a housing 118a that contains a seventh motor. The pitch A link 122 is rotatably coupled to the spherical arm roll link 118. The shaft of the seventh motor is attached to the pitch A link 122 and defines a seventh joint having an axis of rotation G ("axis G") so that when the seventh motor rotates its shaft, the pitch A link 122 pivots about axis G.

Referring to FIG. 1B, the tool driver 128 includes a stage 130 and a carriage 132. The stage 130 is coupled to the carriage by a prismatic joint, such as a track fixed to the stage 130. The tool driver 128 includes one or more motors that drive the carriage 132 along an axis H. The carriage 132 is configured to hold a surgical tool 134 ("tool 134"), which is detachable and replaceable. The tool 134 can be any of a variety of types of surgical tools, and the particular tools depicted in FIG. 1A and FIG. 1B are merely illustrative. In the embodiment of FIG. 1A, an interface portion of the tool 134 is coupled to and located within the carriage 132, while a shaft 136 of the tool 134 extends away from the carriage 132. At the distal end of the tool 134 is an end effector 139 which, in this example, is a clamp. The carriage 132 is also configured to hold a trocar 138. The trocar 138 is detachable and replaceable and has a longitudinal bore through which the shaft 136 of the tool 134 extends. The tool driver 128 may also be configured to rotate the surgical tool 134 around a rotational axis H (also referred to as a "tool axis"). The intersection of the spherical roll axis F, spherical pitch axis G', and the tool axis H constitute the remote center of motion ("RCM") 133 (sometimes referred to as a mechanical RCM) for the trocar 138 and/or the surgical tool 134.

Figure 1C:
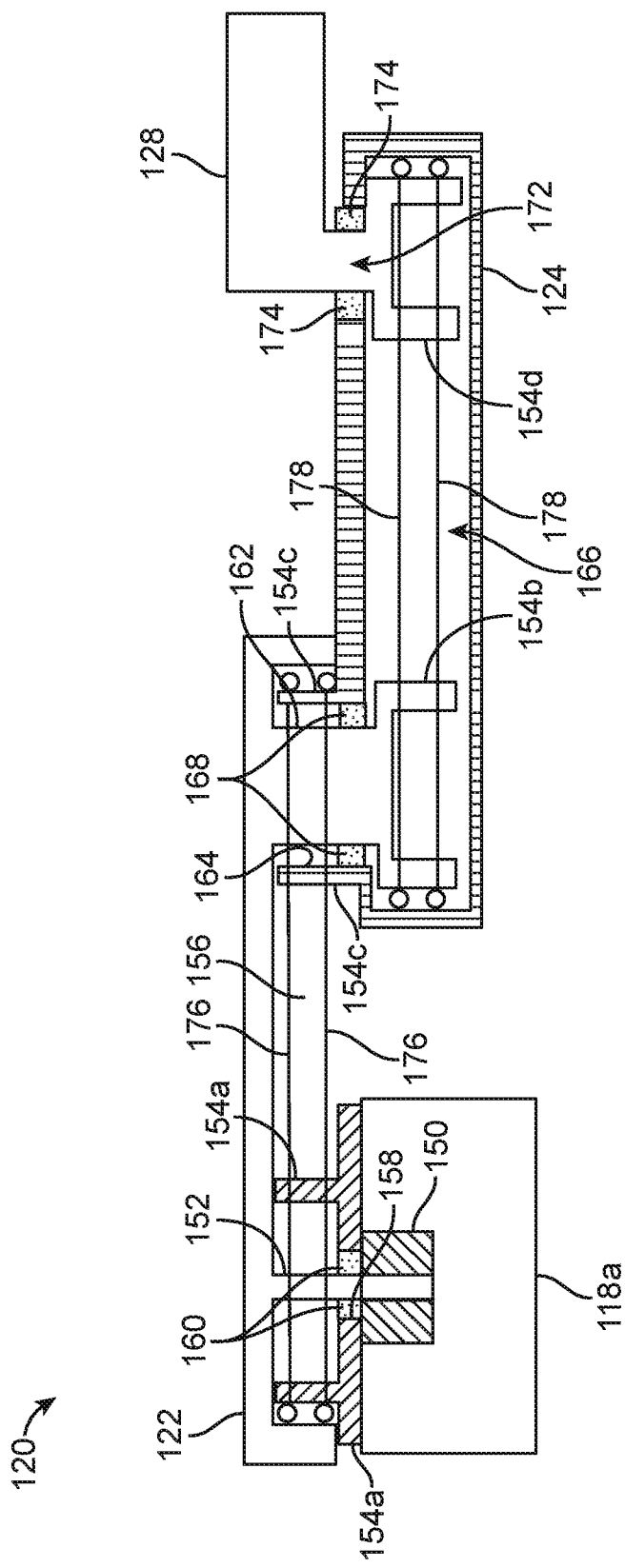
FIG. 1C is a cross sectional view of a pitch assembly, according to an embodiment.

In an embodiment, the pitch assembly 120 is configured so that the axis of rotation defined by the shaft of the seventh motor (axis G) is kept parallel to the pitch axis of rotation of the tool 134 (axis G'). An embodiment of the pitch assembly accomplishes this as shown in FIG. 1C. In FIG. 1C, the seventh motor (labeled 150) is depicted within the housing 118a. The shaft 152 of the seventh motor 150 is attached to the pitch A link 122. A first pulley 154a is attached to the housing 118a such that the first pulley 154a rotates with the housing 118a (but not relative to the housing 118a) and extends into a cavity 156 of the pitch A link 122. The shaft 152 extends through a center bore 158 of the first pulley 154 and engages bearings 160, which are disposed in such a way as to remain in contact with the shaft 152 and an inner surface of the center bore 158.

A second pulley 154b is attached to the pitch A link 122 such that the second pulley 154b rotates with the pitch A link 122 (but not relative to the pitch A link 122) when the pitch A link 122 pivots. A third pulley 154c is attached to the pitch B link 124 such that the third pulley 154c rotates with the pitch B link 124 (but not relative to the pitch B link 124). The third pulley 154c extends into the cavity 156 of the pitch A link 122.

The second pulley 154b includes a shaft 162 that extends into a bore 164 of the third pulley 154c (and into a cavity 166 of the pitch B link 124) and engages bearings 168, which are disposed in such a way as to remain in contact with the shaft 162 and an inner surface of the bore 164.

A fourth pulley 154d is attached to the tool driver 128 such that the fourth pulley 154d rotates with the tool driver 128 when the tool driver 128 pivots but does not move relative to the tool driver 128. The fourth pulley 154d extends into the cavity 166 of the pitch B link 124 through a bore 172 and engages bearings 174, which are positioned in such a way as to remain in contact with the fourth pulley 154d and an inner surface of the bore 172.

One or more properly-tensioned cables 176 are wrapped around the first pulley 154a and the third pulley 154c so that when the seventh motor 150 rotates its shaft 152, the pitch B link 124 moves with the pitch A link 122. Similarly, one or more properly-tensioned cables 178 are wrapped around the second pulley 154b and the fourth pulley 154d so that when the pitch B link 124 rotates, the tool driver 128 moves as well. Instead of cables, other mechanisms such as bands or belts may be employed.

Figure 2A:
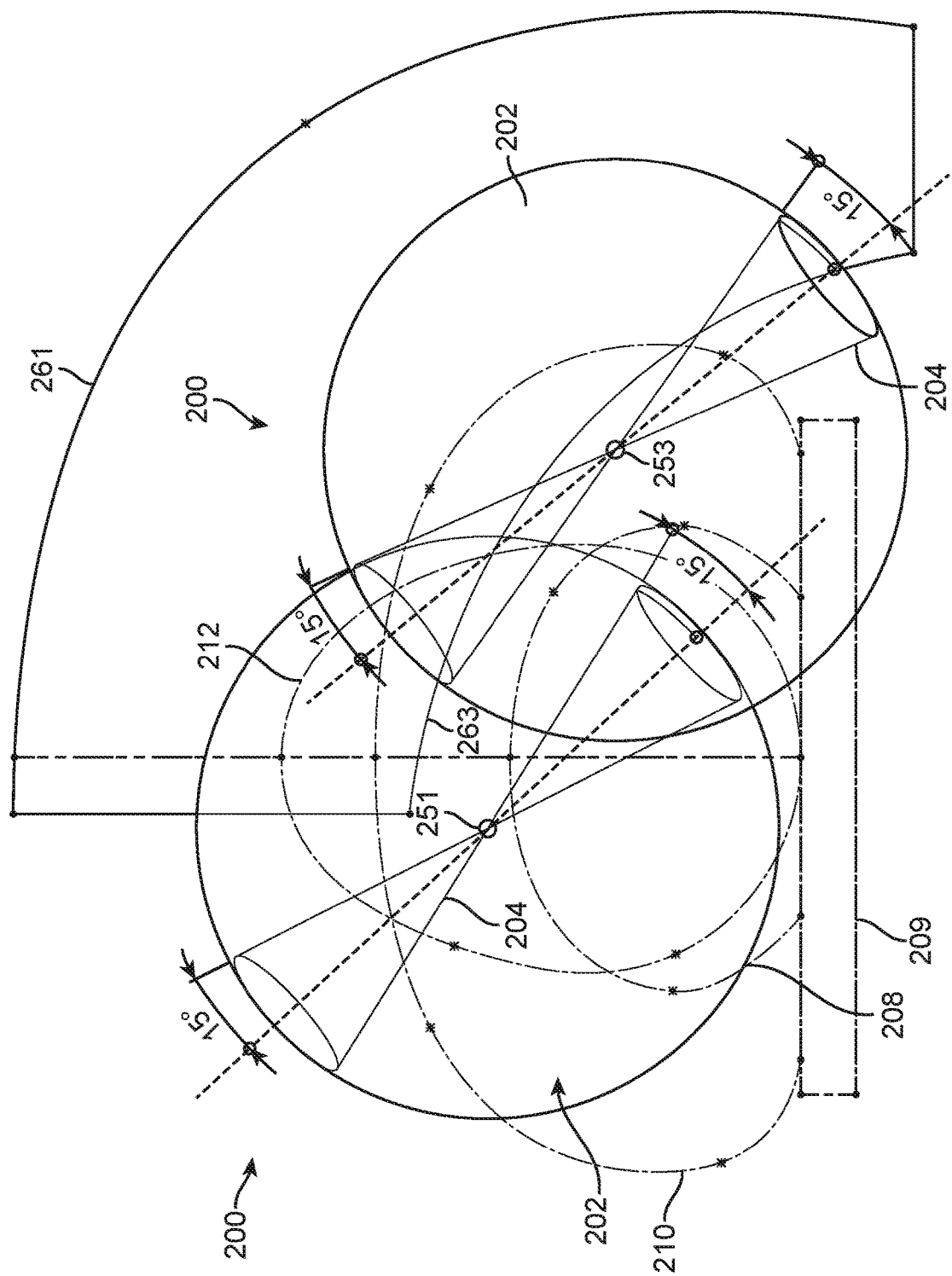
FIG. 2A and FIG. 2B illustrate the range of motion and placement of the remote center of motion for the spherical arm, according to an embodiment.

Turning to FIG. 2A, in an embodiment, the Spherical arm 104 and the tool driver 128 are configured to move the end effector 139 in a workspace defined by a generally spherical volume of space 200 bounded by generally spherical surface area 202. In some embodiments, the volume of space 200 is a sphere, and the surface area 202 is the surface of the sphere. For convenient reference, this volume of space 200 may be referred to as a "sphere 200," though it is to be understood that the volume of space 200 may not be perfectly spherical, but instead may be approximately or generally spherical. A processor controlling the robotic arm 100 can place the surgical tool 134 (in particular the end effector 139) within the space 200 by manipulating the various joints of the spherical arm 104 or the Cartesian arm 102 or both (e.g., transmitting signals to the controllers of the motors). According to an embodiment, the spherical arm 104, in combination with the tool driver 128, can move with four degrees of freedom: (spherical) roll, (spherical) pitch, (tool) translate and (tool) rotate. The first end 104a (base) of the spherical arm 104a may move within an area bounded by a first arc 261 and a second arc 263. The location of the first end 104a within this area, in effect, determines where the sphere 200 is located (i.e., the sphere 200 moves according to the movement of the base of the spherical arm 104).

Figure 2B:
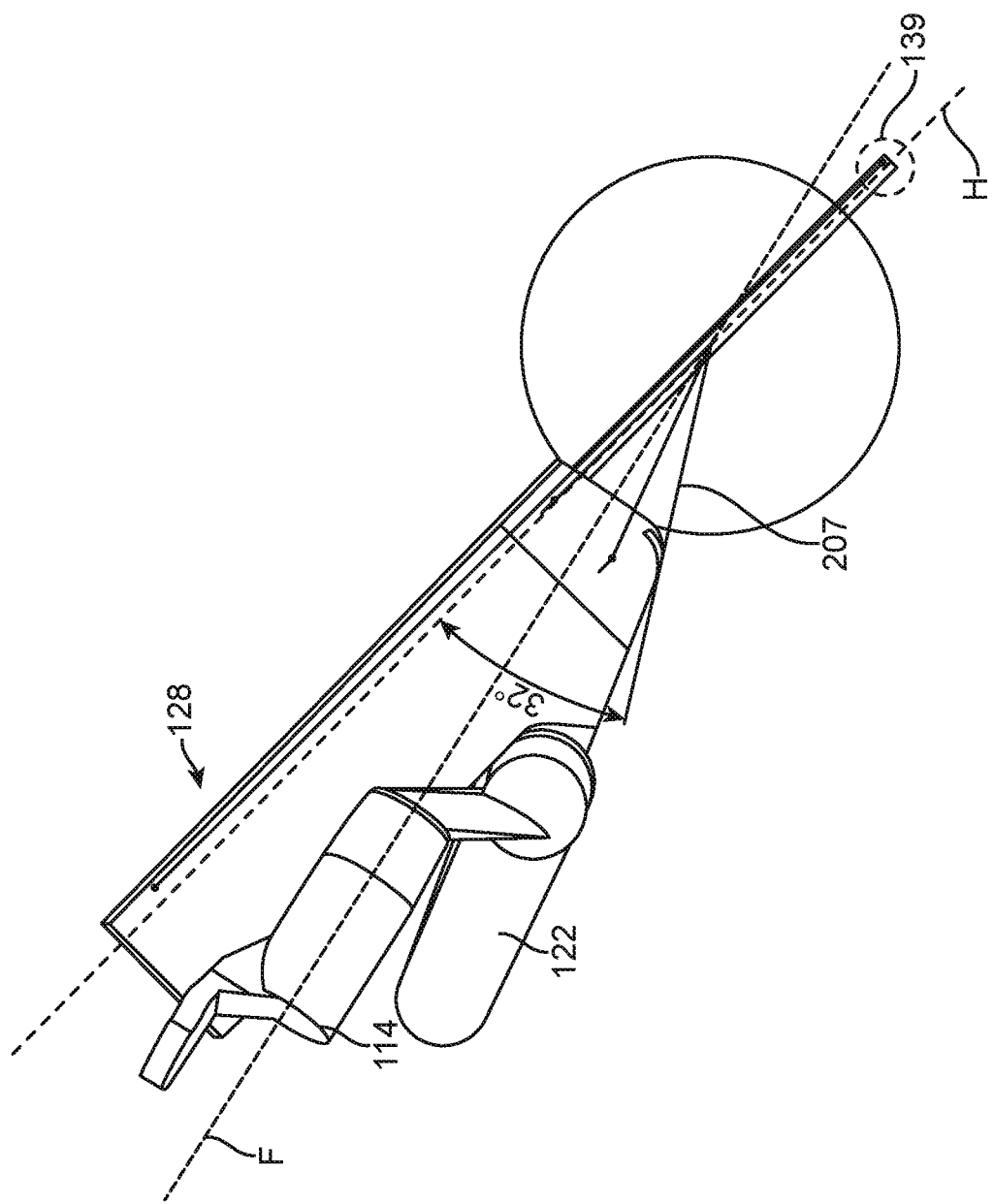

FIG. 2B shows the spherical roll axis F and the tool axis H (tool translate and tool rotate). At this collapsed position, the angle between the tool axis H and the roll axis F is about 15 degrees. This defines the unreachable cone 204 opposite the spherical arm 104. The angle between the tool axis H and a line tangent to the lowest part of the spherical arm 104 (line 207 in FIG. 2B) may be referred to as the patient clearance angle. This defines how close the roll axis E of the spherical arm 104 can be positioned to the surface of the patient. Because the spherical arm 104 occupies the space inside this 32 degree area, it also sets how far the end effector 139 can reach at its opposite extended position (with the end effector 139 reaching back toward the first end 104a of the spherical arm 104).

In some embodiments, the end effector 139 can reach anywhere within the sphere except for the cone 204 (which is about 15 degrees revolved around the spherical roll axis F). Additionally, as shown in FIG. 2B, the end effector 139 may not be able to reach the area of the spherical volume of space 200 occupied by the rest of the spherical arm 104, which can be imagined as a cone 206 of about 32 degrees (revolved around the spherical roll axis F). The cone 206 corresponds to a "patient clearance angle" shown in FIG. 2B. The locations inside the first cone 204 (the 15 degree cone) may be inaccessible because, at these locations, the spherical arm 104 is collapsed as shown in FIG. 2B. To reach locations inside the cone 204, the Cartesian arm 102 can be manipulated (e.g., in response to signals from a processor) so that when the Cartesian arm 102 is repositioned (e.g., only the joints of the Cartesian arm 102, not the base), the cone 204 will also move to some other location (as shown in FIG. 2A). At this point, however, the locations within the cone 204 would now be accessible.

In an embodiment, the robotic arm 100 allows for full tool reach inside a patient's body regardless of the position of the arm exterior to the body cavity and regardless of the port placement on the body surface. To illustrate, FIG. 2A shows dashed lines 208, 210, and 212, which represent different patient sizes and positions in cross section. Specifically, line 208 represents a small patient lying supine (on an operating table or surgical bed 209), line 210 represents a large patient lying supine, and line 212 represents a large patient lying on his or her side. The positions of the RCM (equivalently, the location of the port) can be located on these surfaces or any potential surface between these extremes. The two instances of the sphere 200 in FIG. 2A indicate the reach for the end effector 139 as positioned by an arm 100 attached to the right edge of the surgical bed 209. For example, the leftmost instance of the sphere 200 indicates the reach of the end effector 139 when the arm 100 is configured for surgery via a first port 251 (a "high port" in this instance) and the rightmost instance of the sphere 200 indicates the reach of the end effector 139 when the arm 100 is configured for surgery via a second port 253 (a "low port" in this instance). The spherical arm 104 can be positioned to reach any number of possible ports on a patient, and the two ports depicted in FIG. 2A are merely examples. The axis of each instance of the sphere 200 is also the spherical roll axis F of the spherical arm 104. For low ports, it the spherical arm 104 may be positioned such that the "dead zones" (e.g., the cone 204) are located outside the patient's body. For high ports, the dead zone will likely be inside the body cavity. For many cases, it may be positioned in an area of the body that is not receiving surgical treatment. For more complex cases where the end effector 139 must reach all internal areas of the body, the base (first end 104a) of the spherical arm 104 can be repositioned by the Cartesian arm 102 mid-procedure, resulting in a shift of the dead zone inside the body.

In an embodiment, operation of the robotic arm 100 is controlled by signals from a processor (e.g., a microprocessor, microcontroller, application-specific integrated circuit, field programmable gate array, or other logic circuitry), an embodiment of which is shown in FIG. 3 as processor 350. The processor 350, which may be physically located on the robotic arm itself or in a cart-carried unit, is communicatively linked to a console 352, which itself has a processor. The processor 350 is communicatively linked to a motor controller for each of the joints, depicted in FIG. 2A. In an embodiment, the controllers and the processor have a ring topology and communicate via bus using a proprietary protocol or a standard protocol (e.g., EtherCAT). In FIG. 3, the motor controllers, labeled 354a, 356a, 358a, 360a, 362a, 364a, and 366a are each integrated with respective motors 354b, 356b, 358b, 360b, 362b, 364b, and 366b, which, in turn, are located within the respective housings 106a, 108a, 110a, 112a, 114a, 116a, and 118a. One or more of the housings of the first section 102 and the second section 104 may include a sensor that measures linear force and/or torque on the trocar 138 and/or the surgical tool 134 based on the torque experienced at the motor, and sends signals back to the processor 350 representing the measurement. The sensor is represented in FIG. 3 by sensor 369, though it is to be understood that there may be more than one sensor. The sensor 369 may also be located on the trocar 138 or on the surgical tool 134.

In an embodiment, the combination of the spherical arm 104 and the Cartesian arm 102 allows full reach inside the body regardless of port placement on the surface. Additionally, the Cartesian arm 102 is designed such that it can reach a given port from multiple base mounting positions (e.g., there are four base positions per side of the operating table or surgical bed). This creates flexibility for the staff setting up a robotic arm system with multiple arms (i.e., multiple instances of the robotic arm 100).

According to an embodiment, the Cartesian arm 102 has two additional degrees of freedom that allow movement of the second end 102b of the Cartesian arm 102 (or the base/first end 104a of the spherical arm 104) along the surface 202 of the sphere 200. This design allows flexibility in positioning the various arms so they do not collide with one another or with other objects in the environment.

With multiple arms (i.e., multiple instances of the robotic arm 200), repositioning of the arms is to be accomplished in a way that the arms do not interfere with each other. This gives the ability to reconfigure the "exterior arm shape" so as to avoid collisions with other arms, tools, people, and the environment.

In an embodiment, the robotic arm 100 allows for the dynamic adjustment of the remote center of motion ("RCM") or the location of the port. For example, in an embodiment, the robotic arm 100 can allow the port location to be adjusted dynamically—either through user specification of a certain location for the RCM or through sensing of patient tissue characteristics.

In some situations, the location of the RCM may need to be modified from its 'natural' location, which is determined by the mechanical design of the spherical arm 104. For example, the RCM 133 is depicted in FIG. 1A as the point at which the axes F, G', and H of the spherical arm 104 intersect. If the patient is obese, however, there may not be enough space between the natural remote center and the base of the tool driver 128 (first end 104a of the spherical arm 104) and the attachment point of the trocar 138. It may also be beneficial in very small patients (e.g., in pediatric surgery) to locate the spherical arm 104 further away from the port site than would be allowed if the arm 104 was restricted to operation only about the natural RCM 133.

In such situations, the processor 350 may instruct the arm 100 to move the RCM to a more desirable location. These instructions can cause the arm 100 with all the associated joints to pivot the surgical tool 134 and trocar 138 about the new remote center location. Maintaining a new remote center of motion may require only very small movements of the Cartesian arm 102 joints, which allows the Cartesian arm 102 to operate close to human assistants.

In an embodiment, the location of the RCM 133 can be modified at any appropriate time, and not just at set up time, and can be adjusted from the console 252.

The location of the RCM can be modified by various methods including: (a) manually through a computer interface (i.e. surgeon instructing the robot to change the remote center), (b) automatically, by measuring forces at the trocar and implementing a force-minimizing algorithm, (c) a combination method, where the system alerts the surgeon that excessive forces are being experienced at the trocar. The system may then suggest a new location of the remote center. The surgeon then has the option of reacting to the warning and accepting or modifying the computer suggested location of the remote center.

In an embodiment, the robotic arm 100 has the ability to assume multiple distinct configurations for transport, draping, cart operation, and bed-mounted operation. Because of the various joints on each arm (i.e., each of the Cartesian arm 102 and the spherical arm 104), the system can be configured in multiple ways. This flexibility in configuration allows the robotic arm 100 to be configured in a way that is beneficial for its environment. For example, it may be configured for a small volume for transport.

The Cartesian arm 102 may also allow the robotic arm 100 to perform tasks beyond minimally invasive surgical tool manipulation.

In an embodiment, the base of the tool driver 128 includes a motorized mechanism for attaching and detaching from the trocar 138.

According to an embodiment, the Cartesian arm 102 is configured to move the spherical arm 104 to attach to another port location, as directed by a user at the bedside or from the console 352.

In an embodiment, the Cartesian arm 102 may detach from the trocar 138 and reach a tool reloading station located potentially on a cart from which the arm 100 operates. The arm 100 may then perform an automated tool swap operation before returning to the patient, inserting the surgical tool 134, and redocking to the trocar 138 to continue operation.

In an embodiment, the robotic arm 100 has the ability to overcome non-ideal base mounting locations while still providing full tool reach inside a patient's body. This feature is conveyed by the design of the Cartesian arm 102. The Cartesian arm 102 and its joints are designed in such a way that the Cartesian arm 102 may be mounted in several allowable locations on the surgical bed 209 or on the cart. From these locations, the appropriate parts of the patient's anatomy can still be accessed. This helps to compensate for situations where the base mounting locations on the surgical bed 209 are non-ideal.

According to an embodiment, the robotic arm 100 is designed to reach ports on one half of the largest patients (i.e., left or ride side) from a given side of the surgical bed 209. For smaller patients, an arm on the left side of the surgical bed 209 may reach farther than the patient midline to access ports on the right side of the patient. Since arms can be mounted on both sides of the surgical bed 209, dual-side mounting configurations can address ports on even the largest patient sizes.

In an embodiment, the design of the Cartesian arm 102 allows for establishment of rules of thumb that may be used during setup. For example: (1) For a low port, the Cartesian arm 102 may be attached with the arm 102 folded down below the plane of the surgical bed 209. (2) For a high port, the Cartesian arm 102 may be attached so that it is extended over the surgical bed 209 but the first section of the spherical arm may be pointed down so that the spherical roll axis E intersects the remote center of the desired high port (e.g., a camera port located near the midline of the patient).

For single quadrant procedures (isolated working region inside the body), the arms can be located close together and may be on operated from the cart. For multiquadrant procedures requiring big swings of the arms, an appropriate set up may have two arms on each side of the surgical bed 209. They may be attached to the surgical bed 209 to allow for mid-procedure bed repositioning, or they may be operated from two smaller carts, one on each side of the surgical bed 209.

In an embodiment, the Cartesian arm 102 can only attach to the surgical bed 209 at certain locations. This helps to minimize situations where multiple instances of the arm 102 collide with one another.

Turning again to FIG. 3, in an embodiment, the Cartesian arm 102 includes a handle 368 (also shown in FIG. 1B), which may be coupled to a six degrees of freedom torque sensor 372. The torque sensor 372 senses the torque that a user is exerting in the handle 368 and transmits signals representing the torque to the processor 350. The processor 350, in response, transmits signals to one or more of the joints of the arm 100 (i.e., to the controllers of the motors) to cause the motors to rotate appropriately. This allows the arm 100 to be repositioned by the user via the handle 368. In some embodiments, the user may reposition the arm 100 by manually manipulating the arm 100. Since the Cartesian arm 102 is motorized, movements of the motors are coordinated to move in appropriate ways. If the arm 100 is docked to a trocar, the arm 100 may be repositioned such that the RCM stays fixed in place but the motors of the arm 100 are moved to a more desirable configuration over the patient.

According to an embodiment, the arm 100 is able to move the end effector 139 of the surgical tool 134 in such a way as to avoid creating unsafe motion elsewhere on the arm 100. In an embodiment, the arm 100 (under the direction of the processor 350) accomplishes this while moving the end effector 139 of the surgical tool 134 at speeds comparable to human hand motion and, additionally, not creating unsafe motion of the robotic arm outside the patient (e.g., minimize momentum—moving mass and speed—of the robotic arm).

In an embodiment, the tool driver 128 is short in length (e.g., 12 inches long vs. current on-market lengths of roughly 18 inches). Since the tool driver 128 is short, the rapid pivoting motions about the RCM (which may be necessary for dexterous surgical moves inside the body) result in significantly less momentum (mass of arm times velocity) outside the body. Less momentum means the environment is safer for the surgeons and assistants working near the robot.

In various embodiments, the length of the tool driver is comparable to the length of a human forearm, allowing assistants to reach around the robot arm more easily to access manual ports and tools.

In general, the two part construction of the robotic arm 100 (with the spherical arm 104 and the Cartesian arm 102) prevents large, really fast movement of the portions that are further away from the RCM (i.e., the Cartesian arm 102).

In many procedures, most of the anatomy can be reached by just moving the spherical arm 104. In some cases all of the anatomy can be reached by just moving the spherical arm 104.

The motion of the Cartesian arm 102 to achieve various objectives such as reaching inside the cones (described above) or moving the RCM or carrying out vibration cancellation can be small and limited. This motion is overlaid on the motion of the spherical arm 104. Also, as described above, the fast moving parts of the robotic arm 100 (the spherical arm 104 and the tool driver 128) are small and compact.

Furthermore, because the trocar 138 and the tool driver 128 are narrow (in an embodiment, the mount at the top of the trocar 138 is 1 inch wide and the tool driver 128 is 1.8 inches wide), multiple ports may be positioned close together on the surface of the patient (with multiple instances of the robotic arm 100 working side by side).

Modes of Operation

As can be seen from preceding description, a robotic arm configured according to an embodiment, has multiple joints, which provides increased dexterity. As an example of an outcome of this dexterity, the robotic arm can achieve a specific end effector pose (e.g., pose of the surgical tool 134) in multiple ways. Specifically, the joints can be arranged in multiple configurations to reach the same end effector pose. The dexterity is partially a result of the number of joints. The configuration of the robotic arm is such that it provides redundancy in the degrees of freedom of movement.

According to an embodiment, the robotic arm 100 has multiple control modes. Within each control mode, the robotic arm 100 moves in accordance with certain rules or constraints. Some of these modes will now be described.

Setup Mode

According to an embodiment, in a setup mode, the Cartesian arm 102, together with one degree of freedom (such as spherical roll) of the spherical arm 104, moves the tool driver 128 to achieve a desired position for the trocar 138. This motion moves the RCM 133 in space. The remaining joints in the spherical arm 104 are kept fixed during this mode. By default, these remaining joints are kept at the middle of their respective ranges of motion to maximize workspace, although the user can override the default settings and put the remaining joints in another configuration if needed. The processor 350 and/or the controllers in the respective joints will then maintain those joint values instead.

In an embodiment, the motion commands needed to position the RCM 133 are generated by the processor 350 under command of the operator using some type of user interface such as the handle 368 or some other type of user interface device on the arm. In an embodiment, an X-Y joystick 370 functions (shown in FIG. 3) as the user interface device. As noted above, if a handle is used, it may be equipped with a six degrees of freedom force/torque sensor 372. The forces/torques are read and processed (e.g., by the processor 350) to obtain remote center position and orientation commands (e.g., generated by the processor 350). The arms may be moved into location by using other methods such as backdriving the motors of the joints, etc.

Teleop Mode

According to an embodiment, in a teleop mode, the Cartesian arm 102 is fixed in space, hence preserving the RCM 133. The motion of the end effector 139 is generated by the spherical arm 104 and the tool driver 128.

Repositioning Mode

In an embodiment, in a repositioning mode, the arm 100 (e.g., under control of the processor 350) preserves the RCM of the end effector (e.g., of the surgical tool 134) as well as the pose of the end effector. This is possible by exploiting the two-degree of freedom redundancy gained through the use of the Cartesian arm 102/spherical arm 104 combination. Because of the two degrees of redundancy in the robotic arm, it is possible to move the base (first end 104a) of the spherical arm 104 on the two-dimensional surface 202 (which, as noted above, may be a spherical shell) and maintain the pose of the surgical tool 134.

In the repositioning mode, the user interacts with the robotic arm 100 through a user interface such as the handle 368 which, as noted above, may be coupled with one or more force or torque sensors. The forces and torques are projected onto the sphere 200 (e.g., via software being executed by the processor 350) and the robotic arm 100 would only move in the direction of the projection.

The user may also provide input to the robotic arm 100 to operate in this mode based on motions of a user input device tracked through the console 352. In this case the motion of the user input device would be similarly projected onto the spherical shell (spherical surface 202) to allow the user to interactively reposition the exterior (outside the patient) portion of the robotic arm 100 while maintaining both the RCM 133 and the pose of the surgical tool 134.

Virtual RCM Mode

Normally, during a surgical procedure, the RCM 133 is preserved by fixing the configuration of the Cartesian arm 102 and moving only the spherical arm 104. In an embodiment, however, the robotic arm 100 has a virtual RCM mode, in which the RCM is preserved with a combined motion of the spherical arm 104 and the Cartesian arm 102. This can have several advantages. For example, in bariatric surgery the combined motion can be used to create better clearance between the robot and the patient. The RCM 133 is ideally located close to the internal side of the patient's abdominal wall. For example, in one particular embodiment, due to the geometry of the spherical arm 104, the mechanically constrained RCM 133 needs to be exactly 4.5 inches below the final joint of the pitch assembly 120, and coincident with the surgical tool axis G. For thick abdominal walls, this roughly 4 inches of clearance (between the RCM 133 and the place where the robotic arm 100 docks with the trocar) is insufficient to clear the patient tissue. In these cases, the robotic arm 100 may operate in a virtual RCM mode, in which the "virtual RCM" is not coincident with the "mechanical RCM" defined by the geometry of the spherical arm 104. The virtual RCM can be set further away from the trocar attachment, for example, in order to create more patient clearance. To compensate for this offset between mechanical and virtual RCM, the Cartesian arm 102 moves as the spherical arm 102 moves. By doing this, the robotic arm 100 creates a new "virtual RCM" that is not fixed by the mechanism design (as is the case in the spherical arm 104) but is created by software (e.g., software running on the processor 350). In contrast to the mechanical RCM, the virtual RCM can change either from surgery to surgery or even during surgery. To achieve the latter, an extendable or sliding trocar can be used which can change length mid operation. Alternatively a "collar" may be used to support the shaft of the surgical tool 134 at the trocar attachment location, and the trocar 138 itself may not be attached to the robotic arm 100. Two example cases of the virtual RCM are outlined below.

Case 1—Increasing the reach of tool or tool insertion range. In this case, the mechanical RCM is placed between the virtual RCM and patient anatomy or workspace. By doing so, the surgical tool 134 may be able to reach deeper into a patient's anatomy.

Case 2—Increasing the clearance between robotic arm and the patient's body. In this case, the mechanical RCM is placed between the virtual RCM and base of the carriage (away from the workspace). By doing so, the external swing of the arm may be reduced. This may be particularly useful in patients having an abdominal wall larger than four inches.

Dismount Mode

In an embodiment, the robotic arm may also have a dismount mode for removing the arm from the bed and attaching it to a cart or dolly. To attach the robotic arm to a cart or dolly, the arm may be placed in a particular pose that makes it more convenient for the attachment to occur. The dismount mode puts the arm in this pose. The dismount pose is not a fixed pose and changes as the bed is tilted. Accelerometers in the arm or the bed can sense this degree of tilt and bring the arm in a pose that is compatible for mounting to the cart or dolly. In the case of accelerometer in the bed this mode can also be used to mount the arm on the bed.

Tool Change Mode

In an embodiment, the robotic arm may also have a tool change mode for removing or installing a tool. In this mode, the robotic arm will be capable of moving the surgical tool in or out of the trocar beyond the range of motion available by the last joint to translate the tool. This will allow arms to easily dock or change between trocars in a way similar to how users select trocars during laparoscopy procedures. The tool change mode can also allow for automatic tool change by taking the tool out of the trocar, changing tips, and re-docking to the trocar.

Vibration Compensation Mode

In an embodiment, the robotic arm has a vibration compensation mode. As noted above, the Cartesian arm 102 provides redundant degrees of freedom to control the position and orientation of the trocar 138 around the RCM 133. During normal operation, the Cartesian arm will be able to actively dampen unwanted vibrations caused by flexing of the arm structure, limited stiffness of the arm at the joints, or movement of the table attachment.

Tool Driver and End Effector

Current robotic systems generally have a robotic arm, a sterile barrier enveloping the arm, and a surgical tool. The sterile barrier includes an interface region where mechanical and/or electrical power is transferred from the arm, through the sterile barrier, to the tool to actuate the articulating mechanism of the tool. Typically, each degree of freedom in the articulating mechanism of the tool is driven by an actuator in the arm. If the articulating mechanism of the surgical tool (e.g., the wrist of the tool shown in FIGS. 5A and 5B) is double-acting, such as a hinged joint that rotates both clockwise and counter clockwise in response to input from the user, then the actuator in the arm (e.g., the motors or motor/pushrod combination that pull on the various cables of FIG. 5B) is, in an embodiment, also double-acting (e.g., each cable is pulled by its own, separate motor). Typically this arrangement includes an actuator in the arm with a rotating output, such as the output of a gearmotor, driving a rotating coupling that passes through the sterile barrier without allowing the movement of contaminants across the barrier, and a tool with a rotating input coupling. The rotating input on the tool is connected to the articulating mechanism by a double-acting linkage that is arranged such that clockwise and counter clockwise movement of the input coupling results in a corresponding clockwise or counter clockwise movement of the articulating mechanism. This arrangement is repeated as many times as there are degrees of freedom in the tool.

A fundamental disadvantage of the double-acting actuator-to-tool interface described above is the introduction of backlash, or the complexity and expense of precision interfacing components to minimize backlash. Potential sources of backlash include the gearmotor transmission, the arm side of the sterile barrier coupling, and the tool side of the sterile barrier coupling.

Another disadvantage of the such a double-acting interface is that it creates the need for a rotating coupling crossing the sterile barrier. Unless closed with rotating seals, the coupling opening is a potential path for contamination and pathogens from the non-sterile to the sterile side of the barrier. Further, effective rotating seals add expense and frictional drag to the power transmission through the interface.

Still another disadvantage of such an interface is the need for the double-acting linkage from the tool input to the articulating mechanism. This linkage could be a single rigid link actuated by a crank on the tool input coupling with sufficient stiffness to both push and pull the articulating mechanism without distortion or backlash. More typically the linkage is a loop of flexible material around input and output pulleys, like a belt, chain, or most commonly, a loop of multi stranded metal or polymer cable. In a typical surgical tool with three degrees of freedom, this translates into six cables or linkages transiting the shaft, thereby necessitating a large diameter or thin walled (less stiff) tool shaft. Additionally, pre-tensioning the loop places unwanted loads on the tool shaft and represents a difficult, costly manufacturing step to calibrate tension.

Figure 4A:
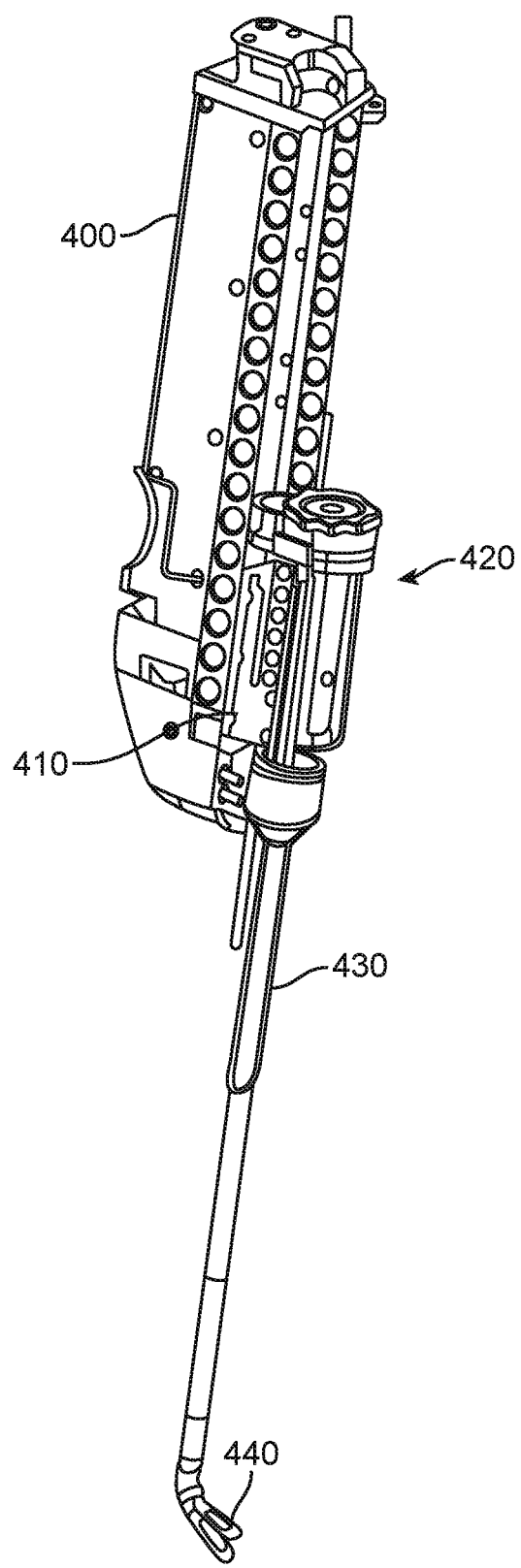
FIGS. 4A-4C are perspective views of a tool driver configured according to an embodiment.
Figure 4B:
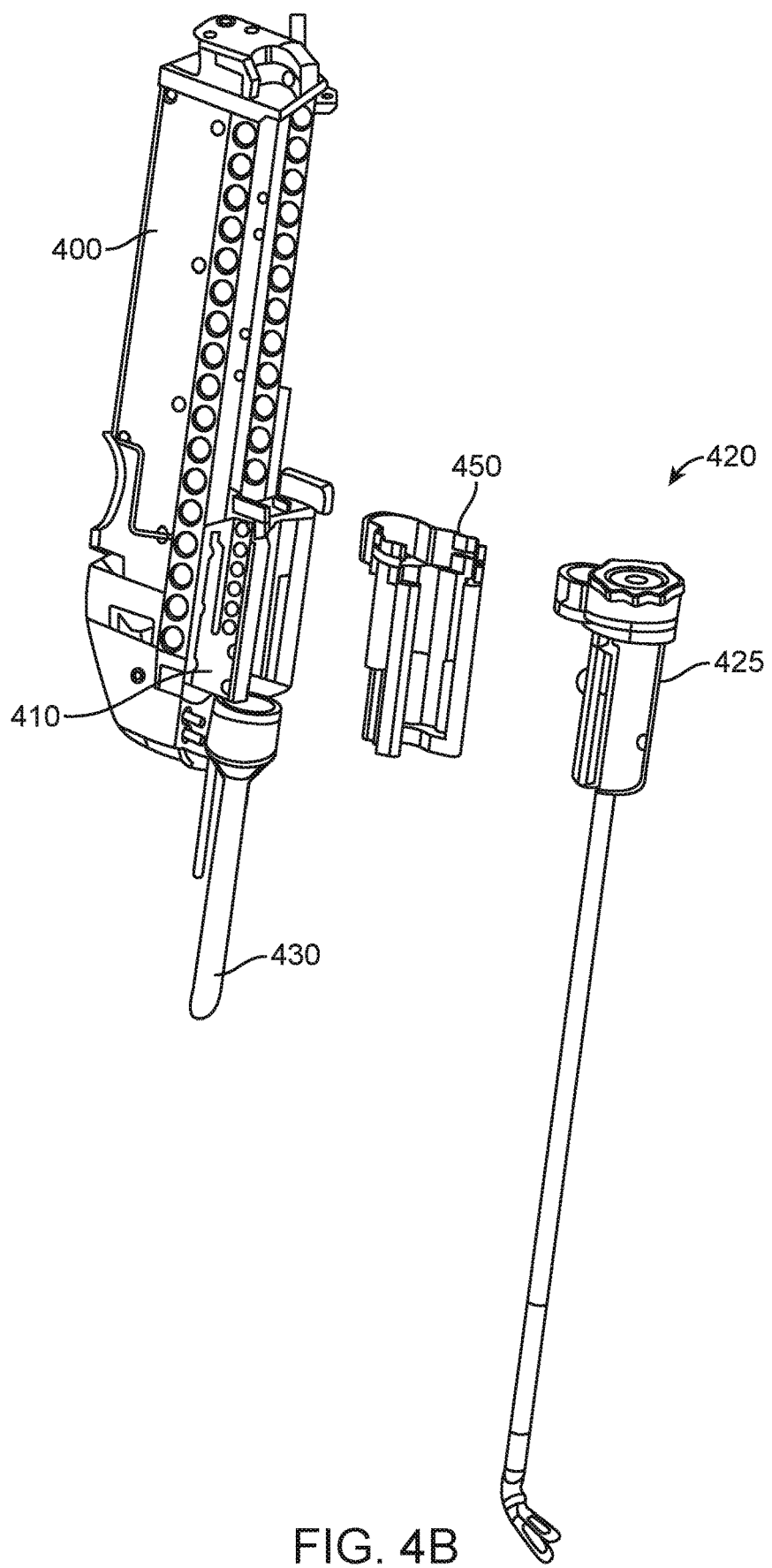

The present disclosure provides a tool driver and end effector that avoids these problems. Turning to FIG. 4A, one possible implementation of the tool driver 128 along with the trocar 138 and the surgical tool 134 will be now be described. The tool driver of FIG. 4A includes a stage 400 and a carriage 410. The carriage 410 slides along the length of the stage 400. The carriage 410 contains portions of the interface to a surgical tool 420, which will be described in more detail below. The surgical tool 420 is disposed with a trocar 430. The surgical tool 420 includes an end effector 440 which, in this example, is a pair of jaws. Other end effectors may be used, however. FIG. 4B shows an exploded view of the members shown in FIG. 4A. In this configuration, the surgical tool 420 has a tool housing 425 that may be coupled to a sterile barrier tool interface 450. This combined group is then coupled to the carriage 410. In an embodiment, the steral barrier is attached to the carriage 410 and the tool 420 is mounted to the entire assembly. The reason for this is that the tool 420 may be exchanged many times during a surgical procedure and sterility needs to be maintained for the duration of the procedure. The couplings will be explained in more detail below.

Figure 4C:
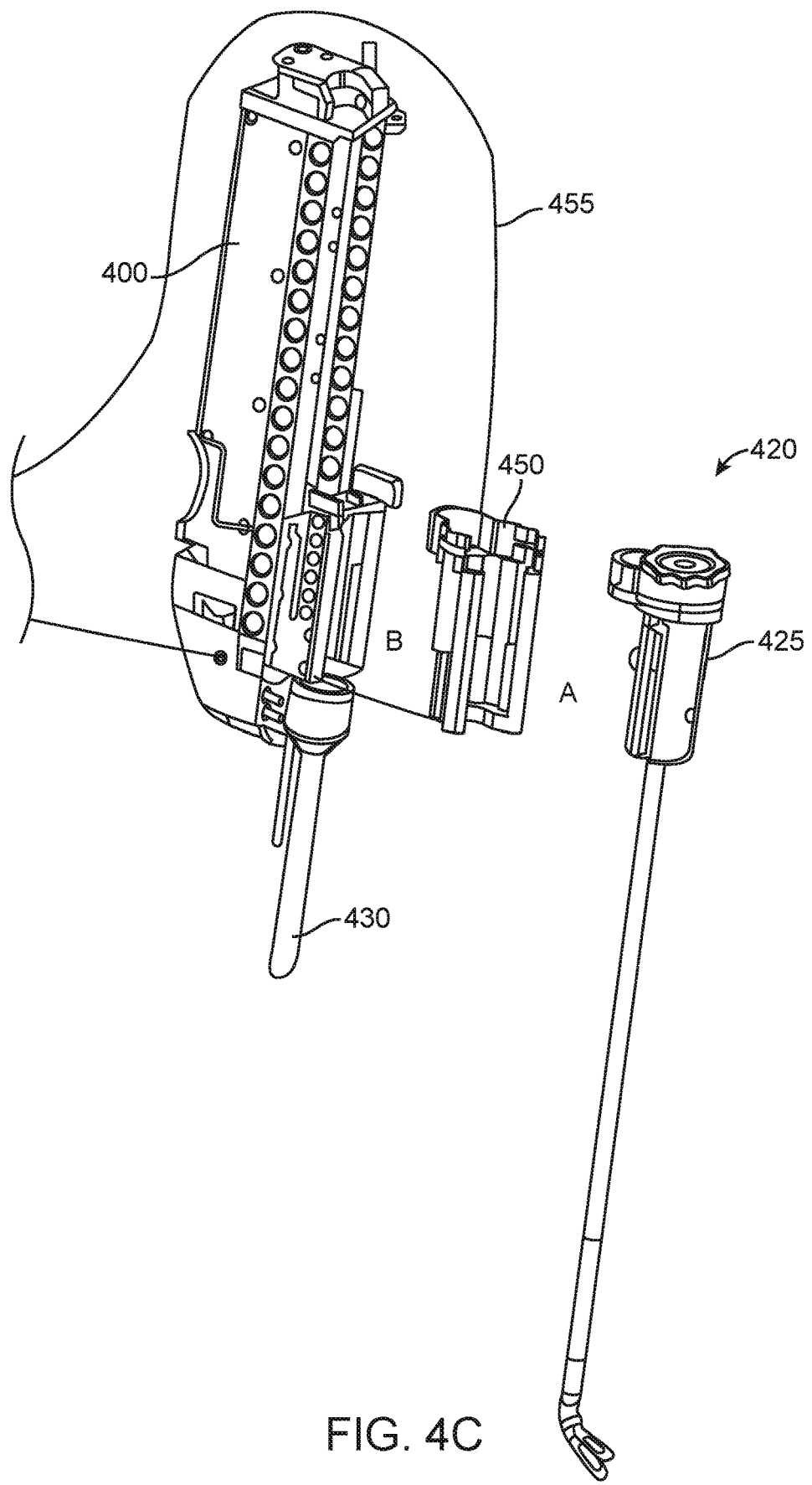

FIG. 4C is the same as FIG. 4B except that FIG. 4C shows a flexible sterile barrier 455 which may be made of various materials such as plastic. The flexible barrier is fixed to the sterile barrier tool interface all along the edge of the interface. With this arrangement, the front side of the sterile barrier tool interface (indicated by the letter A) may be in the sterile field where as the backside of the interface (indicated by the letter B) may be in the non-sterile field. The size and shape of the flexible barrier 455 is such that during a surgical operation, it may be draped over the stage and other portions of the arm. As will be further described below, the flexible barrier is fixed all along the entire edge of the sterile barrier tool interface such that there are no breaks in the sterile barrier, removing any pathways for pathogens to migrate from a non-sterile field to the sterile field. This is in contrast to current techniques that use rotational couplings between an actuator and the tool and where there is a likelihood for pathogens to cross the sterile barrier unless the couplings are sealed. Sealing with rotational couplings may be achieved, but require more complicated manufacturing techniques.

Figure 5A:
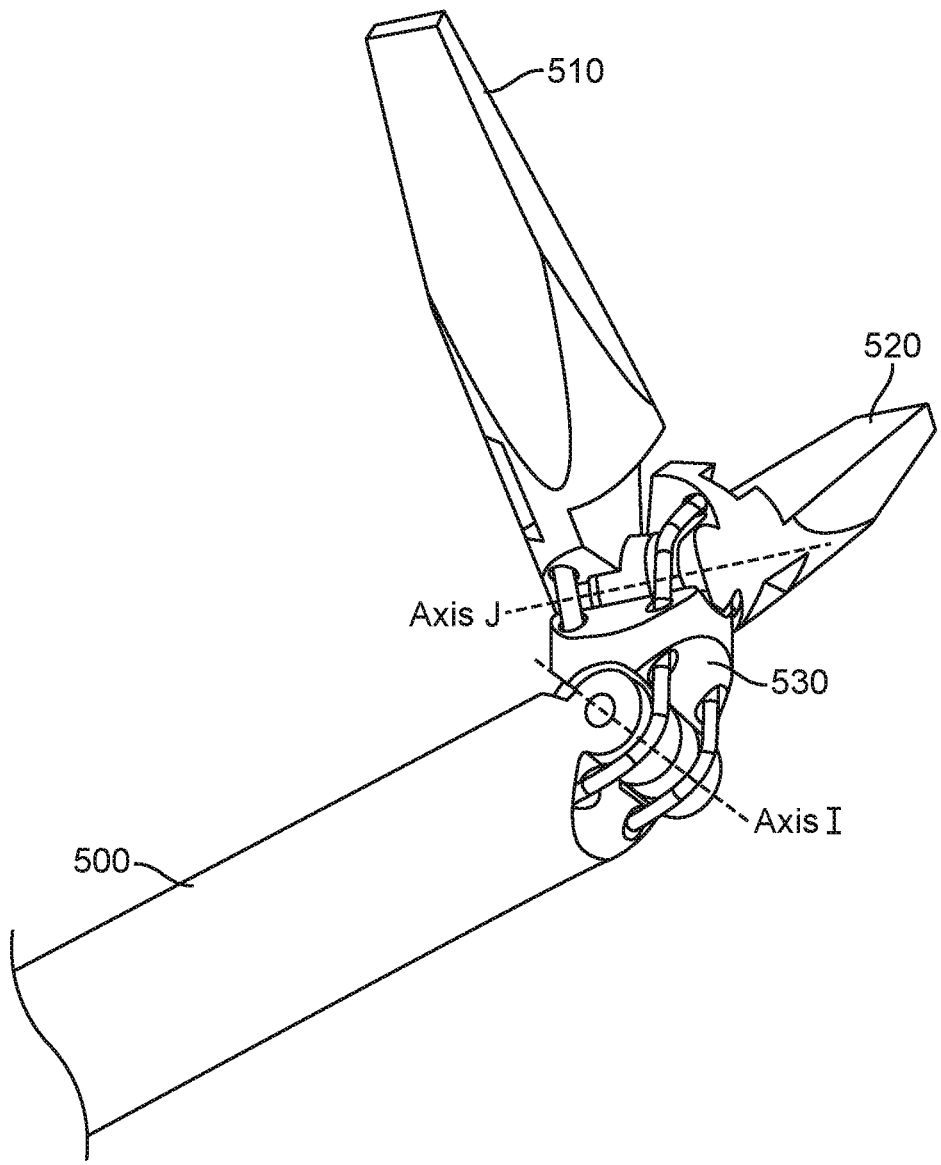
FIG. 5A is a perspective view of an end effector configured according to an embodiment.

Turning to FIG. 5A, one possible implementation of an end effector for a surgical tool is shown. This particular configuration has three degrees of freedom with an antagonistic linkage system comprising four flexible cables. The articulating elements of the end effector include a tool shaft 500, a wrist 530, a first jaw 510, and a second jaw 520 (the first jaw 510 and second jaw 520 form the two sections of end effector 440 illustrated in FIG. 4A). A first degree of freedom is the articulation of the jaws and wrist about Axis I. The second degree of freedom is articulation of the jaw 510 about Axis J. The third degree of freedom is articulation of the jaw 520 about Axis J.

Figure 5B:
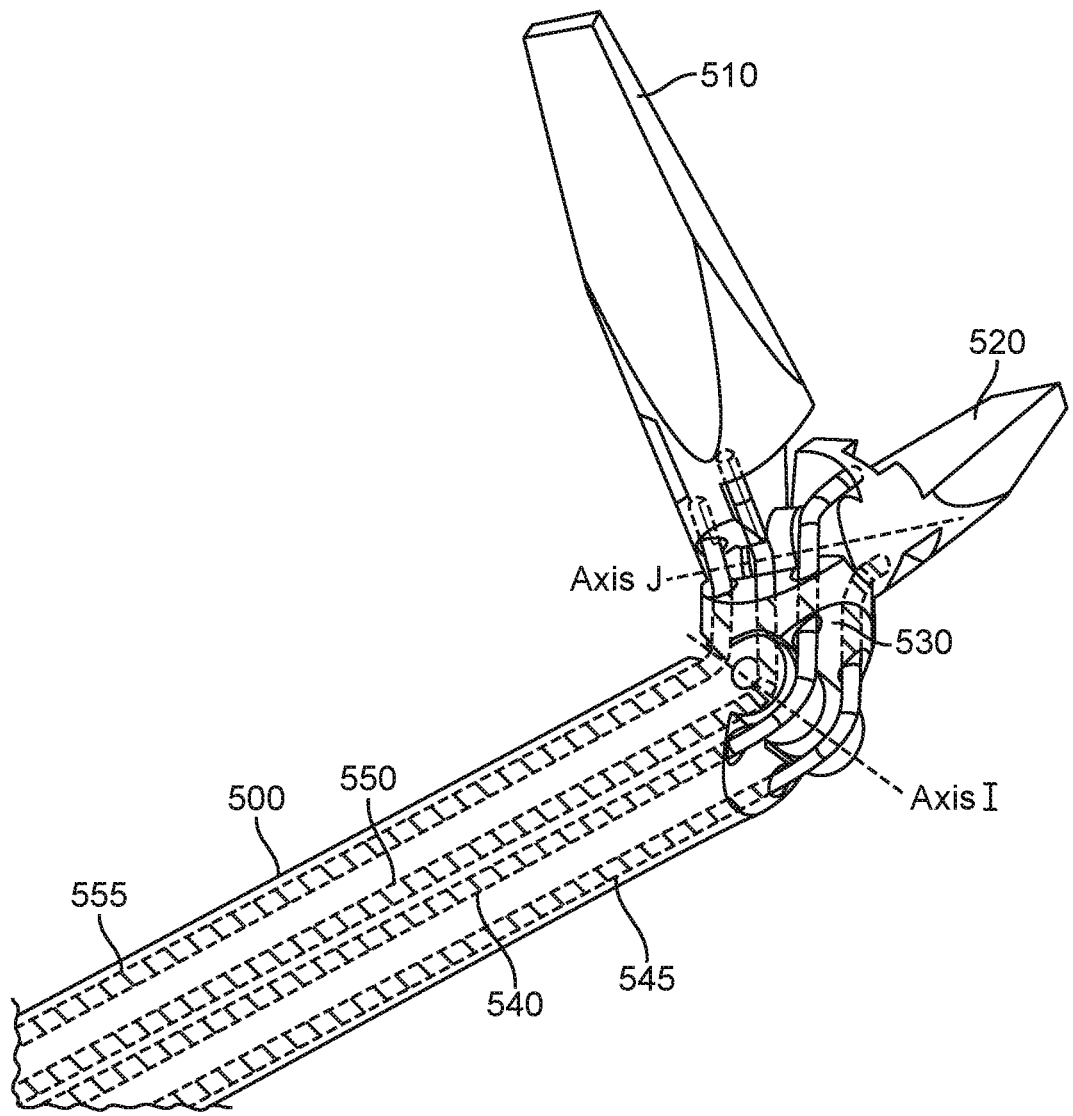
FIG. 5B is a transparent view of the end effector of FIG. 5A.

Turning to FIG. 5B, the arrangement of the four cable linkages according to an embodiment is shown. In this illustration, it can be seen that moving cables 550 and 555 together and allowing cables 540 and 545 to follow (while maintaining pretension) will pitch the wrist and jaws about Axis I. Similarly, keeping cables 540 and 545 fixed while shortening cable 550 and allowing cable 555 to follow (while maintaining pretension) will articulate the jaw 510 about Axis J, and so on. Every position of the three degrees of freedom has a unique cable position solution, noting that all force is applied in tension.

Figure 6A:
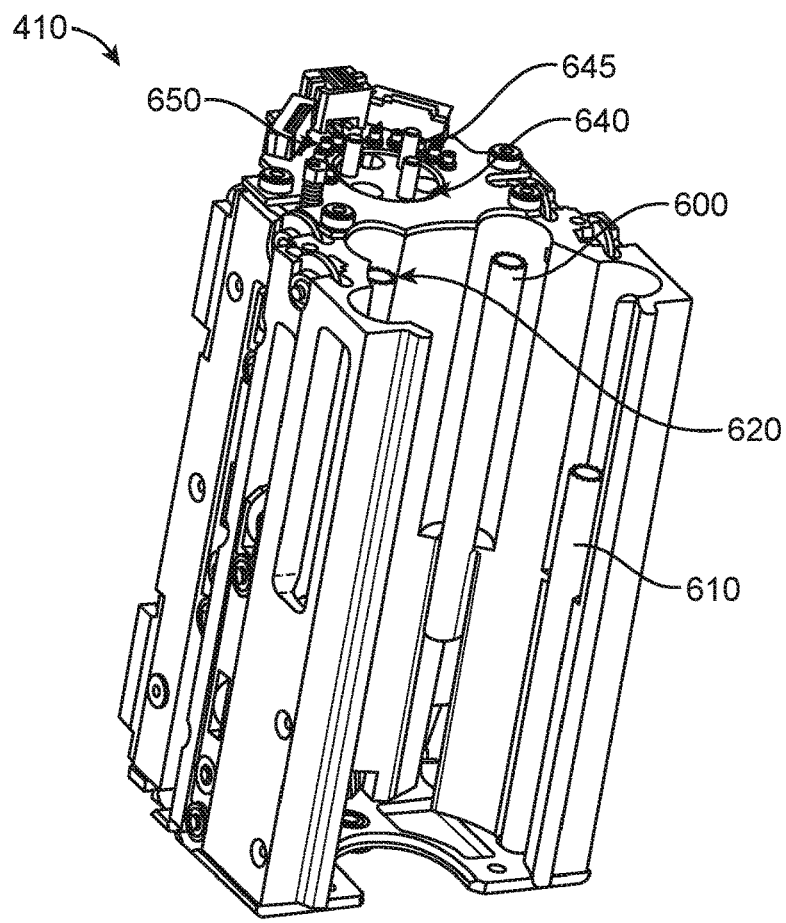
FIG. 6A is a perspective view of a carriage configured according to an embodiment.
Figure 6B:
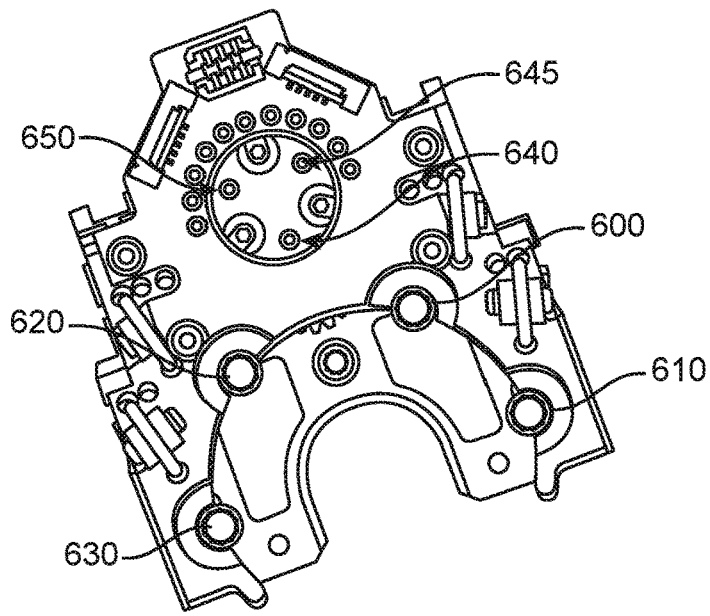
FIG. 6B is a top view of the carriage of FIG. 6A.

FIG. 6A shows details of the carriage 410 that contains a portion of the tool interface. FIG. 6B shows the top view of the carriage. As is illustrated by the figures, the carriage contains a semi-circular cavity within which are arranged four upward acting, linear push rods 600, 610, 620 and 630. These push rods are actuated either directly or indirectly by the same number of force generating actuators. The force generating actuators may include various mechanisms such as, but not limited to, electric motors, driving screw type linear actuators, gearmotors, driving cables with a capstan, hydraulic cylinders, or pneumatic cylinders. In one configuration, electric motors in the arm apply tension to cables.

Figure 7A:
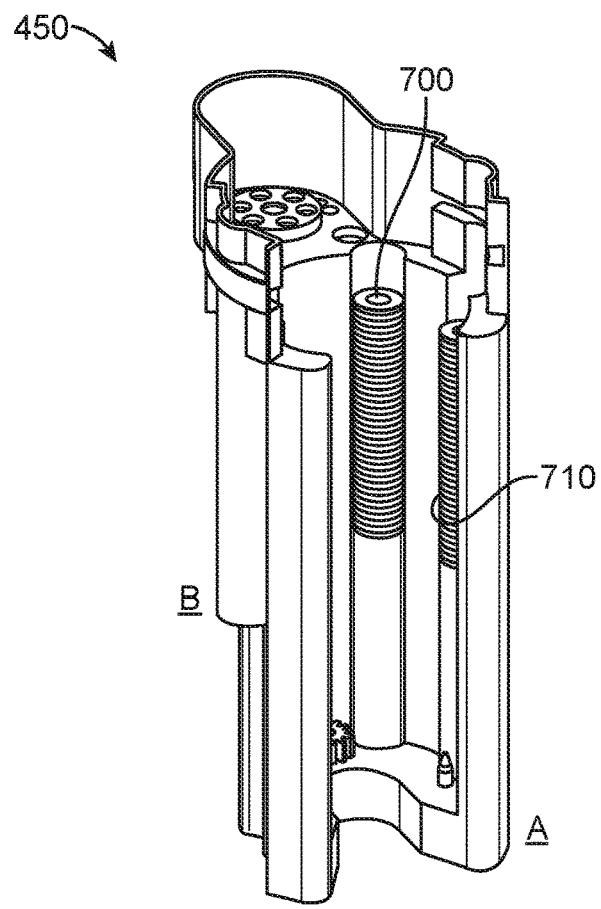
FIG. 7A is a perspective view of a sterile barrier tool interface according to an embodiment.
Figure 7B:
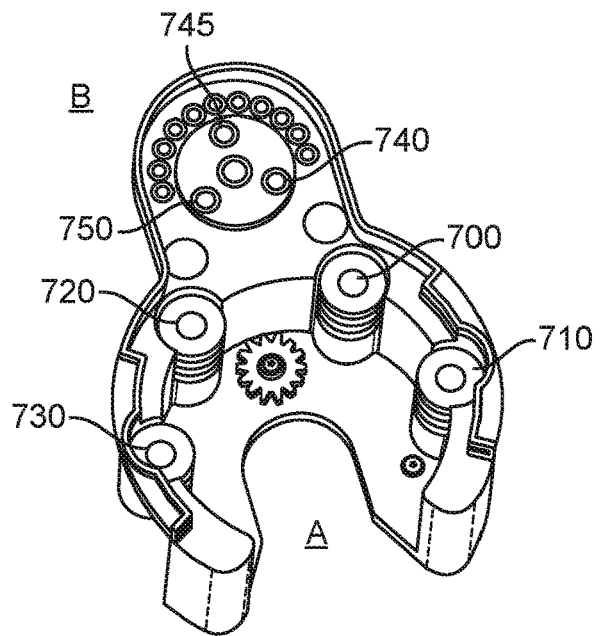
FIG. 7B is a top view of the sterile barrier tool interface of FIG. 7A.

Turning to FIG. 7A, an embodiment of the sterile barrier tool interface 450 is shown. FIG. 7B shows the top view of this interface. As described before, a flexible barrier may be fixed to the sterile barrier tool interface all along the edge of the interface. The body of the sterile barrier tool interface fits into and couples with the semicircular cavity of the carriage 410. The sterile barrier tool interface includes four bellows 700, 710, 720, and 730. When the sterile barrier tool interface is coupled to the carriage, the bellows, which are sealed to the body of the sterile barrier tool interface, are located over the linear push rods 600, 610, 620, and 630. Thus, the linear push rods may move up and down inside the bellows and the bellows may extend and contract depending on the position of the push rods. When the flexible barrier is present, this configuration ensures that side A of the sterile barrier tool interface may remain the sterile side. In alternative configurations, features other than bellows may be used accomplish the same end (to transfer actuation from the arm to the tool), such as an inverting tubular sleeve, or rolling contact interface in place of the push rods and bellows.

Figure 8A:
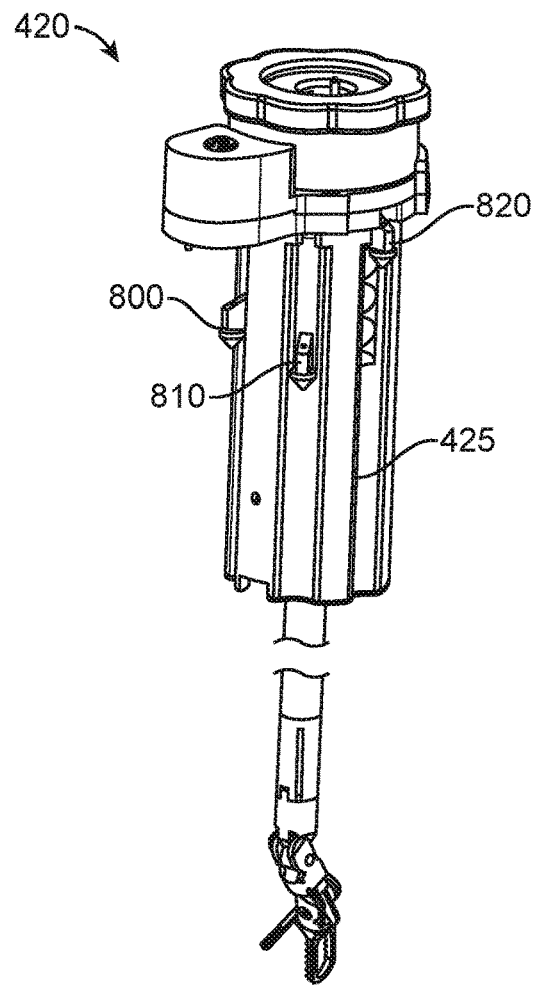
FIG. 8A is a perspective view of a surgical tool configured according to an embodiment.
Figure 8B:
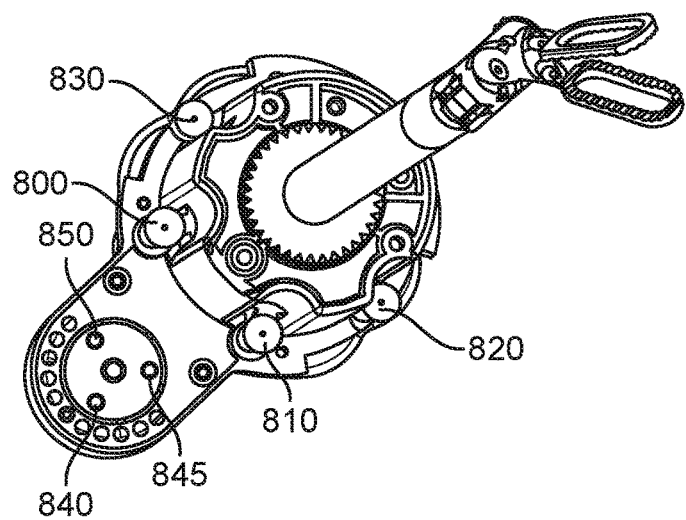
FIG. 8B is a bottom view of a surgical tool configured according to an embodiment.

FIGS. 8A and 8B show an example of the surgical tool 420 according to an embodiment. In this embodiment, the tool housing 425 fits into the sterile barrier tool interface and connects securely to it to resist and counteract actuation loads that are conveyed through linear rods 600, 610, 620, and 630 and bellows 700, 710, 720, and 730. The surgical tool has four input fingers 800, 810, 820, and 830 that are arranged about the body and are connected directly or indirectly to the cables 540, 545, 550, and 555 illustrated in FIG. 5B. When installed into the sterile barrier tool interface 450, the linear push rods 600, 610, 620, and 630 apply upward force on the tool input fingers through the sterile barrier bellows 700, 710, 720, and 730, thereby actuating them without direct contact and maintaining separation between the non-sterile arm and the sterile tool and operating room.

One other aspect of the interface 450 will now be described, related to the electrical connections. Frequently, tools have electrical components such as sensors or electrical actuation systems; these may be powered through the sterile barrier without introducing gaps in the barrier where the barrier may be compromised. Alternatively, such components may be powered through separate cables connecting the tool directly to, for example, a control tower with a tool power supply. The carriage may have spring loaded metallized pins such as pins 640, 645, and 650 (FIGS. 6A and 6B) which may make contact to metallized areas such as 740, 745, and 750 that are located on the sterile barrier tool interface 450 (FIG. 7B). The metallized areas are sealed to the body of the sterile barrier tool interface so that no pathogens may get through. Thus when the sterile barrier tool interface is coupled to the carriage, the metallized areas on the tool interface makes contact to the spring loaded pins of the carriage. Next, the tool may also have metallized spring loaded pins such as pins 840, 845, and 850. When the tool is coupled to the sterile barrier interface, these pins make contact to the metallized areas on the interface. With this configuration the, electrical pass through may be achieved while preserving the integrity of the flexible sterile barrier.

The arm to tool interface described above overcomes some of the disadvantages of current systems. Specifically, the interface described herein has (i) reduced or no backlash, (ii) does not require the interface to penetrate the sterile barrier, (iii) reduces the number of linkages that have to be accommodated by the tool shaft, (iv) reduces the cost and complexity of the tool, and (v) reduces the cost and complexity of the sterile barrier interface region.

Thus it may be seen that the arrangement described above provides an interface that allows the cables in the tool to be actuated antagonistically, without any rotational couplings and be preserving the integrity of the sterile barrier.

According to various embodiments, the robotic arm has the following characteristics: (a) it is designed for minimally invasive surgical procedures, (b) a section of the arm has a kinematic description that contains at least three joints whose axes intersect at one point, such that the axes are not orthogonal (e.g., the arm 100 is never in a configuration where axes F, G, and H in FIG. 1A are all simultaneously orthogonal to one another), and (c) one or more of these axes is defined by a mechanical linkage system such that the axis of the actuator is not coincident with the kinematic axis of the degree of freedom controlled by that actuator.

In an embodiment, the section of the arm described above (referred to as the "second section") is mounted on a section (referred to as the "first section") that may include at least four joints whose axes do not intersect each other and do not intersect the intersection point of the axes of the second section.

In an embodiment, the robotic arm also includes tool driver having at least three additional actuators configured to drive the motion of a removable surgical tool. The tool driver may also include a distal linear joint that allows the surgical tool to operate in a long or a short configuration that can be adjusted by telescoping the surgical tool during a procedure. This feature allows the surgical tool to be used in operating close to the peritoneum or deep in the body without requiring a very long range of motion in the distal joint.

According an embodiment, the robotic arm includes an interface to a surgical tool, in which the interface provides direct linear actuation for at least three degrees of freedom of the tool to simplify the mechanical complexity of the tool.

In an embodiment, the interface integrates force sensors downstream of the transmission to allow combined position and force control algorithms of the surgical tool.

According to various embodiments, there are several possible benefits of the robotic arm and the tool interface described herein, including improved ease of use, a set-up process that is simpler and more logical, more accessibility to the internal organs within the body, fewer constraints on port placement, and the ability for the arm to assume multiple configurations and ability to dynamically adjust the remote center.

According to an embodiment, a robotic arm configured to manipulate a surgical tool comprises: a tool driver configured to hold the surgical tool; a first section comprising a first end coupled to a base, a second end distal from first end; a first link that includes a motor configured to rotate at least a portion of the first section around a pitch axis; a second link coupled to the first link, the second link including a motor configured to rotate at least a portion of the first section around a roll axis; and a second section comprising: a first end coupled to the second end of the first section, a second end distal from the first end, a first link that includes a motor configured to rotate at least a portion of the second section around a roll axis, a second link coupled to the first link, the second link including a motor configured to rotate the tool driver around a pitch axis.

In an embodiment, a robotic arm comprises a first section comprising: a first link including a first motor; a second link coupled to a shaft of the first motor such the rotation of the shaft moves the second link about a first axis, the second link including a second motor; a third link coupled to a shaft of the second motor such the rotation of the shaft moves the third link about a second axis, the third link including a third motor; a fourth link coupled to a shaft of the third motor such the rotation of the shaft moves the fourth link about a third axis, the third link including a fourth motor; a fifth link coupled to a shaft of the fourth motor such the rotation of the shaft moves the fifth link about a fourth axis, the fifth link including a fifth motor; and a second section coupled to the first section, the second section comprising: a first link coupled to a shaft of the fifth motor such the rotation of the shaft moves the first link about a fifth axis, the first link of the second section including a sixth motor; a second link coupled to a shaft of the sixth motor such that the rotation of the shaft moves the second link about a sixth axis, the second link of the second section including a seventh motor, a first pitch link coupled to a shaft of the seventh motor such that the rotation of the shaft pivots the first pitch link about a seventh axis, a second pitch link coupled to the first pitch link; a tool driver configured to hold and move a surgical tool in rotational and translational directions, the tool driver coupled to the second pitch link, wherein a series of cables transfers motion from the seventh motor to the first and second pitch links and to the tool driver.

According to an embodiment, a robotic surgery system comprises: a robotic arm; a tool driver coupled to an end of the robotic arm; a trocar coupled to the tool driver; a surgical tool disposed within the trocar and coupled to the tool driver; and a controller that executes instructions to carry out actions comprising: measuring a force on the trocar or the surgical tool, wherein the trocar and the surgical tool are at least partially disposed within the body of a patient at a surgical site, and changing a remote center of motion of the trocar from a first location to a second location based on the measured force.

The particular implementations shown and described herein are illustrative examples of the disclosure and are not intended to otherwise limit the scope of the disclosure in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

We claim:

1. A robotic arm configured to manipulate a surgical tool, the robotic arm comprising:
    a tool driver configured to hold the surgical tool;
    a first section comprising
    a first end coupled to a base,
    a second end distal from first end,
    a first link that includes a motor configured to rotate at least a portion of the first section around a pitch axis, wherein the pitch axis is the closest axis of rotation to the first end,
    a second link distal to the first link, the second link including a motor configured to rotate at least a portion of the first section around a roll axis that runs in a lengthwise direction of the first section; and
    a second section comprising
    a first end coupled to the second end of the first section,
    a second end distal from the first end,
    a first link that includes a motor configured to rotate at least a portion of the second section around a roll axis,
    a second link distal from the first the second link including a motor configured to rotate the tool driver around a pitch axis, and
    a pitch assembly coupled to the second link of the second section, the pitch assembly comprising
    a first link having a first end rotatably coupled to the second link of the second section and a second end distal from the first end, and wherein the motor of the second link of the second section is configured to rotate the first link of the pitch assembly around the pitch axis, and
    a second link having a first end coupled to the second end of the first link of the pitch assembly and a second end coupled to the tool driver.

2. The robotic arm of claim 1, wherein the second section is configured to move a tip of the surgical tool in the range of motion defined by a volume of space bounded by a spherical surface area.

3. The robotic arm of claim 1, wherein the first section further comprises:
    a third link coupled to the second link, the third link including a motor configured to move at least a portion of the first section around a second pitch axis;
    a fourth link coupled to the third link, the fourth link including a motor configured to move at least a portion of the first section around a second roll axis.

4. The robotic arm of claim 1, wherein the first link of the second section is a spherical arm base link and the second link of the second section is a spherical arm roll link, and the pitch assembly is configured so that the pitch axis defined by a shaft of the motor of the spherical arm roll link remains parallel to a pitch axis of rotation of a tool coupled to the tool driver.

5. The robotic arm of claim 1, wherein
the tool driver comprises carriage configured to hold the surgical tool and a stage coupled to the carriage by a prismatic joint,
the tool driver is configured to move the carriage in a translational direction.

6. The robotic arm of claim 5, wherein the translational direction is along a longitudinal axis of the surgical tool.

7. The robotic arm of claim 1, wherein the second section is configured to move an end effector of the surgical tool within a volume of space bounded by a spherical surface area.

8. The robotic arm of claim 1, wherein the tool driver is configured rotate the surgical tool around an axis of the surgical tool.

9. The robotic arm of claim 1, further comprising a user interface device for receiving input representing motions commands for the robotic arm.

10. The robotic arm of clam 9, wherein the user interface device comprises a handle coupled to the robotic arm.

11. The robotic arm of claim 10, wherein the user interface device further comprises a six degrees of freedom sensor that senses the force on the handle.

12. The robotic arm of claim 9, wherein the user interface device comprises an X-Y joystick.

13. The robotic arm of claim 1, wherein, in a mode of operation,
each of the links of the first section stays in a fixed position,
each of the links of the second section moves in response to user input.

14. A robotic arm comprising:
a first section having a first end operable to be coupled to a base and a second end distal to the first end, the first section comprising:
a first link including a first motor;
a second link coupled to a shaft of the first motor such the rotation of the shaft moves the second link about a first axis, the first axis comprises a first pitch axis and the first pitch axis is the closest axis of rotation to the first end, the second link including a second motor;
a third link coupled to a shaft of the second motor such the rotation of the shaft moves the third link about a second axis, the second axis comprises a roll axis that runs in a lengthwise direction of the first section, the third link including a third motor;
a fourth link coupled to a shaft of the third motor such the rotation of the shaft moves the fourth link about a third axis, the third axis comprises a second pitch axis, the third link including a fourth motor;
a fifth link coupled to a shaft of the fourth motor such the rotation of the shaft names the fifth link about a fourth axis, the fifth link including a fifth motor; and
a second section coupled to the first section, the second section comprising
a first link coupled to a shaft of the fifth motor such the rotation of the shaft moves the first link about a fifth axis, the first link of the second section including a sixth motor;
a second link coupled to a shaft of the sixth motor such that the rotation of the shaft moves the second link about a sixth axis, the second link of the second section including a seventh motor,
a first pitch link coupled to a shaft of the seventh motor such that the rotation of the shaft pivots the first pitch link about a seventh axis, wherein the seventh axis is a pitch axis,
a second pitch link coupled to the first pitch link;
a tool driver configured to hold and move a surgical tool in rotational and translational directions, the tool driver coupled to the second pitch link,
wherein a series of cables, bands, or belts transfers motion from the seventh motor to the first and second pitch links and to the tool driver.

15. The robotic arm of claim 14, wherein a mechanical remote center of motion of the surgical tool is located between a virtual remote center of motion and a patient or surgical workspace.

16. The robotic arm of claim 14, wherein the tool driver comprises a carriage configured to hold the surgical tool and a stage coupled to the carriage by a prismatic joint,
the tool driver is configured to move the stage in a translational direction.

17. The robotic arm of claim 16, wherein the tool driver is further configured to rotate the tool about a longitudinal axis.

18. The robotic arm of claim 16, wherein the mechanical remote center of motion of the surgical tool is located between the virtual remote center of motion and the carriage.

* * * * *